US011292891B2

(12) United States Patent
Anderson

(10) Patent No.: US 11,292,891 B2
(45) Date of Patent: Apr. 5, 2022

(54) RESIN BLENDS CONTAINING A PHTHALONITRILE REACTIVE DILUENT AND A DIPHTHALONITRILE RESIN, PREPREGS, AND ARTICLES

(71) Applicant: 3M INNOVATIVE PROPERTIES COMPANY, St. Paul, MN (US)

(72) Inventor: Benjamin J. Anderson, Eden Prairie, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 246 days.

(21) Appl. No.: 16/491,789

(22) PCT Filed: Feb. 19, 2018

(86) PCT No.: PCT/US2018/018612
§ 371 (c)(1),
(2) Date: Sep. 6, 2019

(87) PCT Pub. No.: WO2018/175025
PCT Pub. Date: Sep. 27, 2018

(65) Prior Publication Data
US 2020/0131336 A1   Apr. 30, 2020

Related U.S. Application Data

(60) Provisional application No. 62/475,396, filed on Mar. 23, 2017, provisional application No. 62/568,157, filed on Oct. 4, 2017.

(51) Int. Cl.
| | | |
|---|---|---|
| C08K 5/315 | (2006.01) | |
| C07C 255/54 | (2006.01) | |
| C08J 5/24 | (2006.01) | |
| C08L 79/00 | (2006.01) | |
| C08K 5/372 | (2006.01) | |
| C08K 7/02 | (2006.01) | |
| C08L 79/02 | (2006.01) | |
| C08J 5/04 | (2006.01) | |
| B32B 27/20 | (2006.01) | |
| B32B 27/28 | (2006.01) | |

(52) U.S. Cl.
CPC ............ C08K 5/315 (2013.01); B32B 27/20 (2013.01); B32B 27/281 (2013.01); C07C 255/54 (2013.01); C08J 5/04 (2013.01); C08J 5/24 (2013.01); C08K 5/3725 (2013.01); C08K 7/02 (2013.01); C08L 79/00 (2013.01); C08L 79/02 (2013.01); C08J 2379/00 (2013.01); C08J 2479/00 (2013.01); C08L 2205/025 (2013.01)

(58) Field of Classification Search
CPC ..... B32B 27/20; B32B 27/281; C07C 255/54; C08J 5/24; C08J 5/04; C08J 2379/00; C08J 2479/00; C08K 5/315; C08K 5/3725; C08K 7/02; C08L 79/00; C08L 79/02; C08L 2205/025
See application file for complete search history.

(56) References Cited

U.S. PATENT DOCUMENTS

| | | |
|---|---|---|
| 3,429,722 A | 2/1969 | Economy |
| 3,496,250 A | 2/1970 | Czerwinski |
| 5,780,154 A | 7/1998 | Okano |
| 8,394,977 B2 | 3/2013 | Tiefenbruck |
| 2016/0168327 A1 | 6/2016 | Keller |

FOREIGN PATENT DOCUMENTS

| | | |
|---|---|---|
| CN | 103694191 | 4/2014 |
| CN | 103756312 | 4/2014 |
| CN | 103664699 | 2/2015 |
| WO | WO 2017-172515 | 10/2017 |
| WO | WO 2017-173040 | 10/2017 |
| WO | WO 2017-173195 | 10/2017 |

OTHER PUBLICATIONS

Bulgakov, "Phthalonitrile-Carbon Fiber Composites Produced by Vacuum Infusion Process", Journal of Composite Materials, Dec. 2017, vol. 51, No. 30, pp. 4157-4164.
Derradji, "Effect of Silane Surface Modified Titania Nanoparticles on the Thermal, Mechanical, and Corrosion Protective Properties of a Bisphenol-A Based Phthalonitrile Resin", Progress in Organic Coatings, Jan. 2016, vol. 90, pp. 34-43.
Derradji, "New Oligomeric Containing Aliphatic Moiety Phthalonitrile Resins: their Mechanical and Thermal Properties in Presence of Silane Surface-Modified Zirconia Nanoparticles", Iranian Polymer Journal, Jun. 2016, vol. 25, No. 6, pp. 503-514.
Derradji, "Thermal and Mechanical Properties Enhancements Obtained by Reinforcing a Bisphenol-A Based Phthalonitrile Resin with Silane Surface-Modified Alumina Nanoparticles", Polymer Composites, Sep. 2017, vol. 38, No. 8, pp. 1549-1558.
Keller, "High Temperature Resorcinol-Based Phthalonitrile Polymer", Polymer, Jun. 2005. vol. 46, No. 13, pp. 4614-4618.
Koysal, "4-(2-Allylphenoxy)Phthalonitrile", Acta Crystallographica. Section E Structure Reports Online, Aug. 2003, vol. 59, No. 8, pp. 1183-1184.

(Continued)

*Primary Examiner* — Patrick D Niland
(74) *Attorney, Agent, or Firm* — Adrian L. Pishko

(57) ABSTRACT

The present disclosure provides a resin blend. The resin blend includes at least one diluent containing a single phthalonitrile functional group and at least one diphthalonitrile resin. Also provided are prepregs including the resin blend impregnated into continuous reinforcing fibers or a cloth. Similarly, the present disclosure provides a molding compound including chopped reinforcing fibers distributed in the resin blend. An article is also provided, which includes polymerization product of the resin blend. An alternative article includes a substrate and a layer of the resin blend disposed on the substrate. The diluent typically improves processability of the resin blend and lowers the softening temperature of the polymerization product of the resin blend.

18 Claims, 3 Drawing Sheets

(56) References Cited

OTHER PUBLICATIONS

Laskoski, Synthesis and Properties of a Bisphenol A based Phthalonitrile Resin, Journal of Polymer Science. Part A, Polymer Chemistry, Sep. 2005, vol. 43, No. 18, pp. 4136-4143.
Sheng, "Synthesis of High Performance Bisphthalonitrile Resins Cured With Self-Catalyzed 4-Aminophenoxy Phthalonitrile", Thermochimica Acta, Feb. 2014, vol. 577, pp. 17-24.
Wang, "Preparation of Self-Promoted Hydroxy-Containing Phthalonitrile Resins by an in situ Reaction", RSC Advances, 2015, vol. 5, No. 127, pp. 105038-105046.
Xu, Self-Cured Phthalonitrile Resin via Multistage Polymerization mediated by Allyl and Benzoxazine Functional Groups, High Performance Polymers, Dec. 2016, vol. 28, No. 10, pp. 1161-1171.
Yang, "Study on Curing Reaction of 4-Aminophenoxyphthalonitrile/ Bisphthalonitrile", Jun. 2010, vol. 21, No. 6, pp. 743-747.
Zhou, "Preparation and Property Comparison of Ortho, Meta, and Para Autocatalytic Phthalonitrile Compounds with Amino Group", Polymers Advanced Technologies, Oct. 2011, vol. 22, No. 10, pp. 1459-1465.
Zou, "Synthesis, Polymerization, and Properties of Allyl-Functional Phthalonitrile", Journal of Applied Polymer Science, Dec. 2014, vol. 131 No. 23, pp. 41203(1-7).
International Search Report for PCT International Application No. PCT/US2018/018612, dated May 9, 2018, 7 pages.

RESIN BLENDS CONTAINING A PHTHALONITRILE REACTIVE DILUENT AND A DIPHTHALONITRILE RESIN, PREPREGS, AND ARTICLES

CROSS REFERENCE TO RELATED APPLICATIONS

This application is a national stage filing under 35 U.S.C. 371 of PCT/US2018/018612, filed Feb. 19, 2018, which claims the benefit of U.S. Application No. 62/475,396, filed Mar. 23, 2017 and U.S. Application No. 62/568,157, filed Oct. 4, 2017, the disclosure of which are incorporated by reference in their entirety herein.

TECHNICAL FIELD

The present disclosure relates to resin blends, including resin blends that improve the processing of diphthalonitrile resins.

BACKGROUND

Temperature resistant polymer networks are critical for an increasing number of industrial market applications. Applications are diverse from building and construction, electronics packaging, energy and power generation, and transportation. As the environmental temperature of an application increases, the number of available materials able to meet requirements shrinks rapidly.

Phthalonitrile (PN) resins are a class of network forming resins that when polymerized supply excellent thermal stability and degradation resistance, yet commercialization of phthalonitrile resin technology and use is hindered by poor processing properties, high cost, and high temperature autoclave cures. Phthalonitrile resins have high melt temperatures due to the rigid structure of many phthalonitrile molecules which incorporate a large percentage of aromatic structures to maintain the thermal performance of the phthalonitrile polymerized network. The phthalonitrile moiety is also rigid and planar and has a tendency to crystallize. These molecular structure attributes contribute to the high melt temperature of multifunctional PN resins. The high cost of the resin is driven by resin synthesis which utilizes higher cost starting materials (similar to anhydride and imide resins) and multistep synthesis routes. A high glass transition temperature of the polymerized resin imparts excellent thermal stability at high service temperatures, but also contributes to the need for high temperature multistep autoclave cures under inert atmosphere to achieve near full conversion.

SUMMARY

Resin blends are described that provide improved processing of diphthalonitrile resins. In a first aspect, a resin blend is provided. The resin blend includes at least one diluent comprising a single phthalonitrile functional group and at least one diphthalonitrile resin. The at least one diluent comprises a compound of formula I:

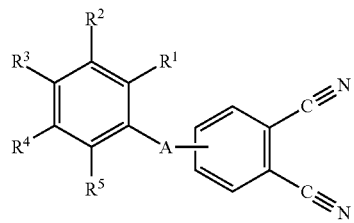

wherein $R^1$, $R^2$, $R^3$, $R^4$, and $R^5$ are independently selected from H, an allyl group, a $C_1$ to $C_{20}$ alkyl group, an aryl group, an ether group, a thioether group, an aldehyde group, a ketone group, an ester group, an amide group, an acid group, a sulfonyl, a halogen, a nitro, a secondary amine group, a tertiary amine group, or a combination thereof; and wherein A is oxygen or sulfur.

In a second aspect, a prepreg is provided. The prepreg includes continuous reinforcing fibers and the resin blend according to the first aspect impregnated into the continuous reinforcing fibers.

In a third aspect, another prepreg is provided. The prepreg includes a cloth and the resin blend according to the first aspect impregnated into the cloth.

In a fourth aspect, a molding compound is provided. The molding compound includes chopped reinforcing fibers distributed in the resin blend according to the first aspect.

In a fifth aspect, an article is provided. The article includes a polymerization product of the resin blend according to the first aspect.

In a sixth aspect, another article is provided. The article includes a substrate and a layer of the resin blend according to the first aspect disposed on the substrate.

Figure 1:
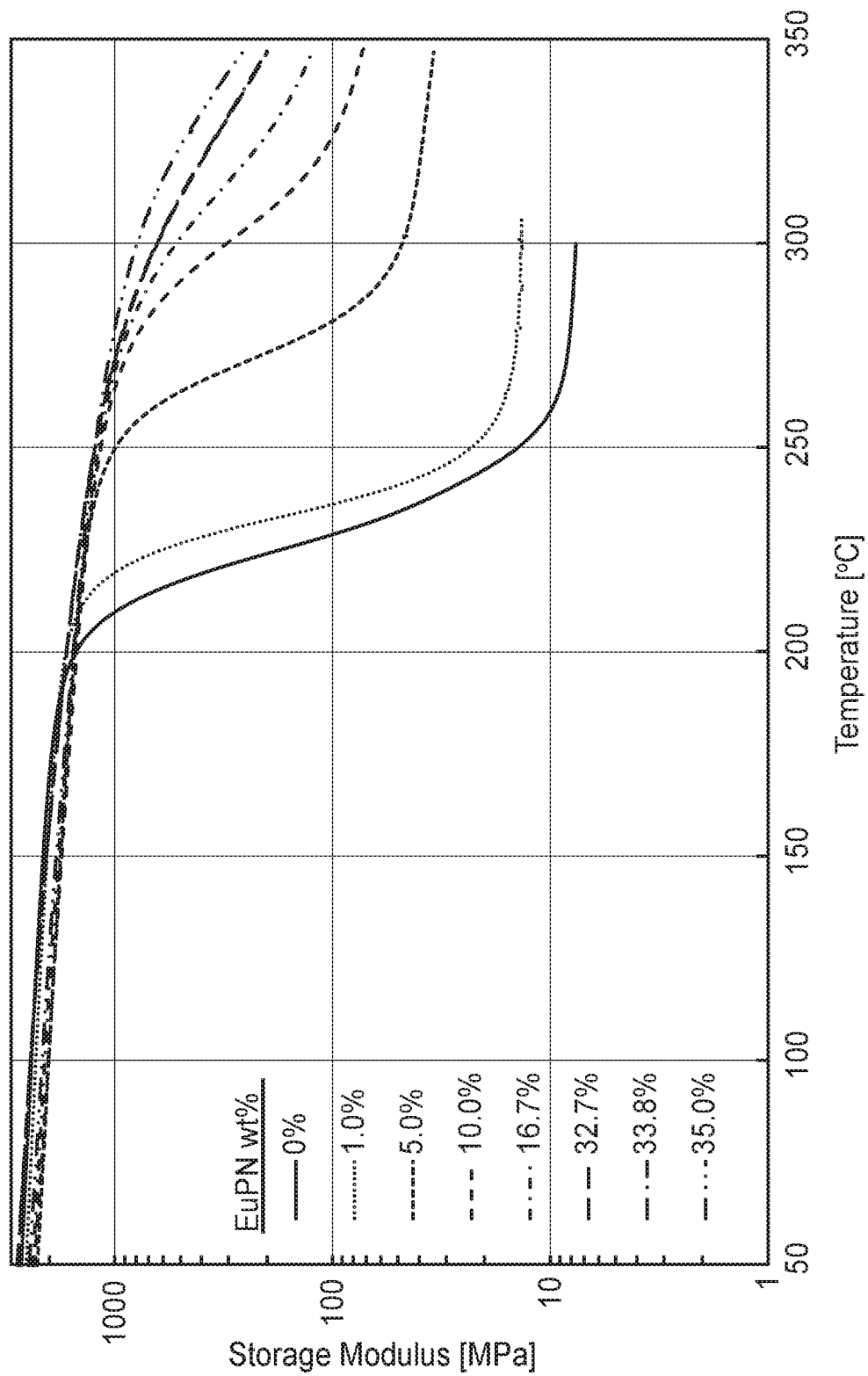
FIG. 1 is a plot of storage modulus versus temperature for BMPN blended with varying weight percent of EuPN and cured with 4,4'-(1,3-phenylenedioxy)dianiline.

While the above-identified figures set forth embodiments of the disclosure, other embodiments are also contemplated, as noted in the specification. The figures are not necessarily drawn to scale. In all cases, this disclosure presents the invention by way of representation and not limitation. It should be understood that numerous other modifications and embodiments can be devised by those skilled in the art, which fall within the scope of the principles of the invention.

DETAILED DESCRIPTION

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "and/or" means either or both. For example "A and/or B" means only A, only B, or both A and B.

As used in this specification, the recitation of numerical ranges by endpoints includes all numbers subsumed within that range (e.g., 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in some embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

As used herein, the term "phthalonitrile" is inclusive of compounds having the characteristic benzene derivative having two adjacent nitrile groups. In the illustrated phthalonitrile group, R is for instance and without limitation, ether, thioether, aryl, alkyl, halogen, amine, ester, or amide, heteroalkyl, or (hetero)hydrocarbyl.

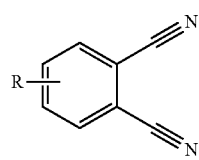

As used herein, "bisphenol M diphthalonitrile ether" refers to bis(3,4-dicyanophenyl) ether of bisphenol M.

As used herein, "bisphenol T diphthalonitrile ether" refers to bis(3,4-dicyanophenyl) ether of bisphenol T.

As used herein, "bisphenol P diphthalonitrile ether" refers to bis(3,4-dicyanophenyl) ether of bisphenol P.

As used herein, "resorcinol diphthalonitrile ether" refers to bis(3,4-dicyanophenyl) ether of resorcinol.

As used herein, "monofunctional phthalonitrile" refers to a compound having a single phthalonitrile group.

As used herein, "multifunctional phthalonitrile" refers to a compound having two or more phthalonitrile groups, preferably two phthalonitrile groups.

As used herein, "alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

As used herein, "allyl" includes a monovalent group having the formula $H_2C=CH-CH_2-$.

As used herein, the term "heteroalkyl" includes both straight-chained, branched, and cyclic alkyl groups with one or more heteroatoms independently selected from S, O, Si, P, and N, and both unsubstituted and substituted alkyl groups. Unless otherwise indicated, the heteroalkyl groups typically contain from 1 to 20 carbon atoms. "Heteroalkyl" is a subset of "hetero(hetero)hydrocarbyl" described below. Examples of "heteroalkyl" as used herein include, but are not limited to, methoxy, ethoxy, propoxy, 3,6-dioxaheptyl, 3-(trimethylsilyl)-propyl, 4-dimethylaminobutanyl, and the like. Unless otherwise noted, heteroalkyl groups may be mono- or polyvalent.

As used herein, "aryl" is an aromatic group containing 6-18 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

As used herein, "(hetero)hydrocarbyl" is inclusive of (hetero)hydrocarbyl alkyl and aryl groups, and hetero(hetero)hydrocarbyl heteroalkyl and heteroaryl groups, the later comprising one or more catenary oxygen heteroatoms such as ether or amino groups. Hetero(hetero)hydrocarbyl may optionally contain one or more catenary (in-chain) functional groups including ester, amide, urea, urethane and carbonate functional groups. Unless otherwise indicated, the non-polymeric (hetero)hydrocarbyl groups typically contain from 1 to 60 carbon atoms. Some examples of such (hetero)hydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl" and "heteroaryl" supra.

As used herein, the term "polymerized product" refers to the result of a polymerization reaction of a polymerizable composition.

As used herein, the term "residue" is used to define the (hetero)hydrocarbyl portion of a group remaining after removal (or reaction) of the attached functional groups, or the attached groups in a depicted formula. For example, the "residue" of butyraldehyde, $C_4H_9$—CHO is the monovalent alkyl $C_4H_9$—. The residue of phenylene diamine $H_2N$—$C_6H_4$—$NH_2$, is the divalent aryl —$C_6H_4$—.

As used herein, a "particle" has an aspect ratio of less than 50:1 of the largest dimension to the smallest dimension, and excludes fibers. As used herein, "nanoparticle" refers to a particle having a D90 particle diameter below 1 micrometer (e.g., "submicron"). As used herein, "particle diameter" refers to the largest dimension of a particle. A suitable method to determine the particle diameter of a nanometer scale particle includes transmission electron microscopy (TEM). As used herein, "microparticle" refers to a particle having a D90 particle diameter below 1 millimeter. A suitable method to determine the particle diameter of a micrometer scale particle includes dynamic light scattering. As used herein, "D90" refers to 90 percent of a population of particles having a particle diameter below the particular particle diameter value.

As used herein, "nanofiller" refers to an additive included in a resin blend that has at least two dimensions (of height, width, and length) that are less than 1 micrometer. As used herein, "microfiller" refers to an additive included in a resin blend that has at least two dimensions (of height, width, and length) that are less than 1 millimeter.

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

Diluents (e.g., reactive diluents) are typically used in resin formulations to alter the properties of a monomer resin or polymer network in a beneficial way. Diluents can be added to monomer resin formulations as a rheological modifier to improve processing of the resin (e.g., alter the viscosity of the resin and alter thermal transitions). Also, diluents can be added to improve end use properties of the polymer network (e.g., one or more of modulus, strength, toughness, adhesion, elongation, chemical resistance, or thermal transitions). The application and utility of monofunctional phthalonitrile compounds as diluents in multifunctional phthalonitrile resins and resin blends for the generation of phthalonitrile polymerized polymer networks is described and demonstrated herein. The monofunctional phthalonitrile compounds operate as diluents in multifunctional phthalonitrile resins by lowering the resin blend viscosity, which is beneficial for lower temperature processing of phthalonitrile resins.

Diluents tend to be monofunctional resins and have a lower molecular weight than the multifunctional resins to which they are added. The lower molecular weight of the (e.g., reactive) diluent generally lowers the viscosity of the resin system and often alters the properties of the polymerized network. The diluents of the present disclosure incorporate monofunctional phthalonitriles with and without a pendent allyl, which are miscible with the multifunctional phthalonitrile resins. Monofunctional phthalonitrile compounds of diverse chemical branching off the third and fourth carbon of the phthalonitrile functional aromatic ring are commonly used as starting materials in the production of dyes and pigments and may be useful starting points for preparing suitable diluents.

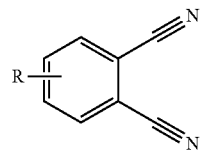

In a first aspect, a resin blend is provided. The resin blend comprises at least one diluent comprising a single phthalonitrile functional group and at least one diphthalonitrile resin. The at least one diluent comprises a compound of formula I:

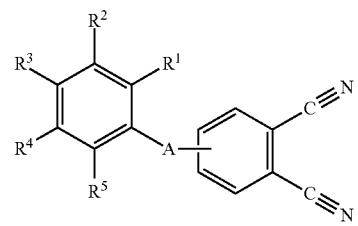

wherein $R^1$, $R^2$, $R^3$, $R^4$, and $R^5$ are independently selected from H, an allyl group, a $C_1$ to $C_{20}$ alkyl group, an aryl group, an ether group, a thioether group, an aldehyde group, a ketone group, an ester group, an amide group, an acid group, a sulfonyl, a halogen, a nitro, a secondary amine group, a tertiary amine group, or a combination thereof; and wherein A is oxygen or sulfur. In certain embodiments, A is preferably oxygen.

In some embodiments, the at least one diluent comprises a compound of formula II:

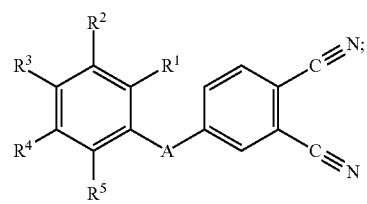

wherein $R^1$, $R^2$, $R^3$, $R^4$, $R^5$, and A are each as defined above with respect to formula I.

In embodiments in which a diluent comprises a monofunctional phthalonitrile without a pendent allyl group, $R^1$, $R^2$, $R^3$, $R^4$, and $R^5$ are independently selected from H, a $C_1$ to $C_{20}$ alkyl group, an aryl group, an ether group, a thioether group, an aldehyde group, a ketone group, an ester group, an amide group, an acid group, a sulfonyl, a halogen, a nitro, a secondary amine group, a tertiary amine group, or a combination thereof; and wherein A is oxygen or sulfur. One suitable monofunctional phthalonitrile diluent without pendent allyl groups includes the compound of formula III:

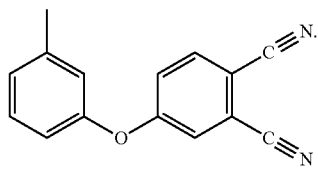

III

Another suitable monofunctional phthalonitrile diluent without pendent allyl groups includes the compound of formula IV:

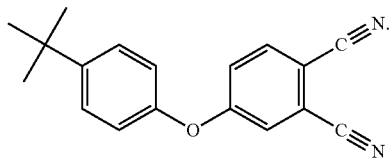

IV

The compound of formula III may be referred to as 4-(3-methylphenoxy)phthalonitrile, and the compound of formula IV may be referred to as 4-(4-tert-butylphenoxy)phthalonitrile.

In embodiments in which a diluent comprises a monofunctional phthalonitrile with a pendent allyl group, $R^1$, $R^2$, $R^3$, $R^4$, and $R^5$ are independently selected from H, an allyl group, a $C_1$ to $C_{20}$ alkyl group, an aryl group, an ether group, a thioether group, an aldehyde group, a ketone group, an ester group, an amide group, an acid group, a sulfonyl, a halogen, a nitro, a secondary amine group, a tertiary amine group, or a combination thereof, with the proviso that one or more of $R^1$, $R^2$, $R^3$, $R^4$, and $R^5$ is an allyl group; and wherein A is oxygen or sulfur. One suitable monofunctional phthalonitrile diluent with pendent allyl groups includes the compound of formula V:

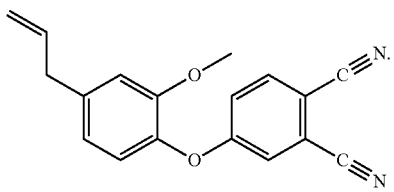

V

Another suitable monofunctional phthalonitrile diluent with pendent allyl groups includes the compound of formula VI:

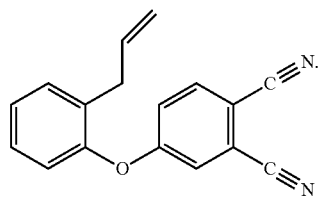

VI

The compound of formula V may be referred to as 4-(2-methoxy-4-allylphenoxy)phthalonitrile or eugenol phthalonitrile. The compound of formula VI may be referred to as 4-(2-allylphenoxy)phthalonitrile or allylphenol phthalonitrile. Accordingly, in some embodiments, the one or more diluents comprise at least one compound selected from the group of 4-(2-methoxy-4-allylphenoxy)phthalonitrile, 3-(2-methoxy-4-allylphenoxy)phthalonitrile, 4-(2-allylphenoxy)phthalonitrile, 3-(2-allylphenoxy)phthalonitrile, 4-(4-tert-butylphenoxy)phthalonitrile, 3-(4-tert-butylphenoxy)phthalonitrile, 4-(3-methylphenoxy)phthalonitrile, 3-(3-methylphenoxy)phthalonitrile, 4-(2-allyl-6-methylphenoxy)phthalonitrile, 3-(2-allyl-6-methylphenoxy)phthalonitrile, 4-(4-acetophenoxy)phthalonitrile, 3-(4-acetophenoxy)phthalonitrile, 4-phenoxyphthalonitrile, 3-phenoxyphthalonitrile, 4-(4-allyl-2,6-dimethoxyphenoxy)phthalonitrile, 3-(4-allyl-2,6-dimethoxyphenoxy)phthalonitrile, 4-(2,6-dimethoxyphenoxy)phthalonitrile, 3-(2,6-dimethoxyphenoxy)phthalonitrile, 4-(nonylphenoxy)phthalonitrile, 3-(nonylphenoxy)phthalonitrile, 4-(3-pentadecylphenoxy)phthalonitrile, 3-(3-pentadecylphenoxy)phthalonitrile, 4-(4-(methylsulfonyl)phenoxy)phthalonitrile, 3-(4-(methylsulfonyl)phenoxy)phthalonitrile, 4-(3-(trifluoromethyl)phenoxy)phthalonitrile, 3-(3-(trifluoromethyl)phenoxy)phthalonitrile, 4-(4-cyanophenoxy)phthalonitrile, 3-(4-cyanophenoxy)phthalonitrile, 4-(pentafluorophenoxy)phthalonitrile, 3-(pentafluorophenoxy)phthalonitrile, 4-(4-(methylmercapto)phenoxy)phthalonitrile, 3-(4-(methylmercapto)phenoxy)phthalonitrile, 4-(4-methylbenzenethio)phthalonitrile, 3-(4-methylbenzenethio)phthalonitrile, 4-(4-tert-butylbenzenethio)phthalonitrile, 3-(4-tert-butylbenzenethio)phthalonitrile, 4-(4-chlorobenzenethio)phthalonitrile, 3-(4-chlorobenzenethio)phthalonitrile, 4-(benzenethiol)phthalonitrile, 3-(benzenethiol)phthalonitrile, 4-(4-nitrophenoxy)phthalonitrile, 3-(4-nitrophenoxy)phthalonitrile, 4-(2-naphthoxy)phthalonitrile, 3-(2-naphthoxy)phthalonitrile.

The design and use of (e.g., reactive) diluents has rarely been applied to multifunctional phthalonitrile monomer resins and their polymerized networks. This likely has to do with the extreme thermal conditions required to polymerize the monomer resin and the difficulty to design a diluent for these conditions. Historically, phthalonitrile resins have required high processing temperatures (near and in excess of 200° C.) to melt the resins and achieve liquid resins with a processable viscosity, temperatures that are not suitable for lower molecular weight reactive diluents due to volatilization and degradation. In addition, after gelation of the resin, post cure temperatures well in excess of 300° C. and approaching 400° C. for extended periods of time will lead to volatilization of residual unbound diluent and degradation of the diluent, which may employ a chemistry that is more susceptible to thermal degradation than the polymerized phthalonitrile network.

Monofunctional phthalonitriles according to the present disclosure may be synthesized by nucleophilic substitution of a nitro group on the third or fourth carbon of the phthalonitrile aromatic ring by a phenoxide or benzenethiolate anion. The nucleophilic substitution can also be performed with a halogen on the third or fourth carbon of the phthalonitrile aromatic ring. Monofunctional phthalonitrile-allyl compounds are not commercially available, and there has been limited synthesis reported of these materials.

The diluents, when added to multifunctional phthalonitrile resins, are shown in at least certain embodiments of the present disclosure to (1) reduce the resin viscosity; (2) reduce the cure cycle time of the resin polymerization; (3) avoid high temperature post cures of greater than 325° C.;

and/or (4) modify the softening temperature of the polymerized network as compared to the multifunctional phthalonitrile resin or resin blend.

The monofunctional phthalonitrile diluents have a lower melt temperature and a lower viscosity than the multifunctional phthalonitrile resins to which they are added. The addition of one or more monofunctional phthalonitrile diluents to multifunctional phthalonitrile resins improves the processing properties of the resin, including lowering the resin system viscosity and suppressing the melt temperature. The monofunctional phthalonitrile diluents are lower in molecular weight than the multifunctional resins, which translates into a lower resin viscosity compared to the multifunctional resin. The lower viscosity of the multifunctional resin with the diluent offers improved processing of the resin in applications that require a low resin viscosity, increases the resin processing temperature window by enabling lower viscosity at lower temperatures, and improves compounding of the resin with fillers and the filler loading capacity.

The application of one or more monofunctional phthalonitrile diluents containing at least one allyl group (e.g., monofunctional phthalonitrile-allyl diluents) to multifunctional phthalonitrile resins and resin blends that produce lower softening temperature polymerized networks is described and demonstrated herein. It has been discovered that during phthalonitrile polymerization, the allyl moiety participates in a secondary polymerization event that results in an elevation of the polymer network softening temperature, leading to polymer networks with higher thermal stability than the neat phthalonitrile resin. Monofunctional phthalonitrile-allyl diluents exhibit an ability to participate in a secondary polymerization mechanism unique to the allyl. This is evidenced by differential scanning calorimetry (DSC), which shows an increased heat of reaction above the phthalonitrile polymerization when the allyl is present (see, e.g., Table 3 in the examples), and the disappearance of the allyl functional group during resin polymerization witnessed by FTIR spectroscopy. It is understood that allyl polymerization is not common and is considered difficult to polymerize in high yield. Thus, poly(allyl) polymers have seen little development.

Initiation of phthalonitrile polymerization has been found to activate allyl polymerization. This is evidenced by the inability of the allyl to react until initiation of phthalonitrile polymerization. The monofunctional phthalonitrile-allyl diluents of the present disclosure do not readily polymerize in the absence of phthalonitrile polymerization, as shown by heating the resin blend up to a temperature of 250° C. and monitoring the resin by DSC. The monofunctional phthalonitrile-allyl diluents did not show evidence of a polymerization reaction exotherm, and were therefore stable and not autocatalytic towards polymerization. This may imply that the initiation of phthalonitrile polymerization that results in the formation of a poly(iminoisoindolenine) is catalytic towards allyl polymerization or reactive with the allyl moiety. The mechanism for the allyl reaction is presently not known.

The secondary polymerization of the allyl has a beneficial impact on the cycle time for resin polymerization. The monofunctional phthalonitrile-allyl diluents, when added as a component resin to multifunctional phthalonitrile resins, reduced the cure time and temperature of polymer network formation compared to traditional multifunctional phthalonitrile resins. Traditional phthalonitrile resin technology requires multiple isothermal cure temperatures totaling 24-48 hours to complete polymerization of the phthalonitrile resin. Typically, a resin polymerization sequence involves an initial five- to six-hour isothermal heating by subjection to a temperature of 200-250° C., followed by subjection to multiple isothermal post-cure temperatures starting at 250° C. and increasing to 400° C. [Laskoski, M., D. D. Dominguez, and T. M. Keller, *Synthesis and properties of a bisphenol A based phthalonitrile resin*. Journal of Polymer Science Part A: Polymer Chemistry, 2005. 43(18): p. 4136-4143; and Keller, T. M. and D. D. Dominguez, *High temperature resorcinol-based phthalonitrile polymer*. Polymer, 2005. 46(13): p. 4614-4618.] In comparison, addition of monofunctional phthalonitrile-allyl diluents to one exemplary multifunctional phthalonitrile resin, BMPN, enabled the resin system to be polymerized by subjection to an initial five-hour isothermal heating at 200° C. and a single four-hour isothermal post-cure at 300° C., totaling a polymerization cycle time of 9 hours (excluding thermal ramps). Use of the ultimate 300° C. post-cure temperature enables the polymerization to be performed without the use of an autoclave, which would be required at temperatures greater than 300° C. Analysis of the linear dynamic mechanical response of the polymerized network measured at one hertz (Hz) as a function of temperature revealed an E' onset temperature and a tan d peak (e.g., tan δ peak) temperature of 290° C. and 350° C., respectively. (See Example 1 below.)

The secondary polymerization of the allyl had a beneficial impact on the softening temperature of the polymerized network. The monofunctional phthalonitrile-allyl diluents, when added to multifunctional phthalonitrile resins, increased the softening temperature of the polymerized network compared to the polymerized network of the multifunctional phthalonitrile base resin. The allyl polymerization mitigated a reduction in the crosslink density caused by the addition of a monofunctional reactive diluent, which lowers the network softening temperature and reduces the network thermal stability. In contrast, this was shown to apply to monofunctional phthalonitrile diluents that lack the allyl pendent group and cannot participate in a secondary polymerization mechanism. The addition of 4-(4-tert-butylphenoxy)phthalonitrile to a difunctional phthalonitrile resin system (i.e., Example 8) led to a reduction of the polymer network softening temperature of 55° C. (i.e., from 243° C. down to 188° C.) and lower thermal degradation resistance as evidenced by thermal weight reduction. In comparison, the addition of eugenol phthalonitrile, a monofunctional phthalonitrile-allyl diluent, to the same difunctional phthalonitrile resin system (i.e., Example 7) not only maintained the softening temperature of the polymerized multifunctional phthalonitrile network but also increased the softening temperature of the network 76° C. (i.e., from 243° C. up to 319° C.). The higher softening temperature of the network increased the use temperature of the polymer by mitigating a loss in mechanical stiffness with temperature. The thermal degradation resistance of the network was maintained as evidenced by thermal weight reduction measurement as a functional of temperature compared to the corresponding multifunctional phthalonitrile polymerized network.

A hindrance towards the development and use of previously modified phthalonitrile systems is the generation of hybrid networks that have lower thermal stability than networks formed from only multifunctional phthalonitrile resin alone. This has been true for epoxy-phthalonitrile hybrids, phenolic-phthalonitrile hybrids, and benzoxazine-phthalonitrile hybrids. Some work has begun to employ the use of allyl pendent groups on multifunctional phthalonitrile resins. These resins have utilized diphthalonitrile ether of 3,3-diallyl-bisphenol A and phthalonitrile terminated benzoxazine resins with allyl pendents. [Xu, M., K. Jia, and X. Liu, *Self-cured phthalonitrile resin via multistage polymerization mediated by allyl and benzoxazine functional groups*. High Performance Polymers, 2016. 28(10): p. 1161-1171; and Zou, X., et al., Synthesis, polymerization, and properties of the allyl-functional phthalonitrile. Journal of Applied Polymer Science, 2014. 131(23): 41203.] The diphthalonitrile ether of 3,3-diallyl-bisphenol A has shown autocatalytic properties toward phthalonitrile polymerization without the addition of a curative or catalyst; the monofunctional phthalonitrile resins with allyl pendents of the present invention were not autocatalytic toward cure. Autocatalysis of the diphthalonitrile ether of 3,3-diallyl-bisphenol A is problematic for synthesis, processing, application and shelf life of the monomer resin due to premature polymerization of the resin. The diphthalonitrile ether of 3,3-diallyl-bisphenol A requires higher temperatures during processing and polymerization than resins that utilize reactive phthalonitrile-allyl diluents. Multistage post-cures up to a temperature of 360° C. were used to polymerize the resin which leads to decomposition during post cure.

The usefulness of monofunctional phthalonitrile-allyl diluents is further demonstrated by applying the diluents to multifunctional phthalonitrile resins and resin blends that have recently been developed to enable lower temperature curing phthalonitrile resins and out of autoclave processing. These multifunctional phthalonitrile resin systems result in polymer networks with softening temperatures (i.e., E'(onset) temperature) between 200 to 300° C. that remove the need for higher temperature long time post cures of up to 400° C., which are undesirable due to premature degradation of the polymer during the post cure and the required use of an autoclave at these elevated temperatures. The lower temperature multifunctional phthalonitrile polymerized networks with softening temperatures between 200 to 300° C. may be cured out of autoclave at a final post cure temperature of 325° C. and below. When curing these phthalonitrile polymerized networks, it has been experienced that full cure of the resin requires the final post-cure temperature to exceed the characteristic mechanical tan d peak temperature of the fully cured network. Addition of monofunctional phthalonitrile-allyl diluents to these same multifunctional phthalonitrile resins and resin blends preserved the ability to polymerize the resin at a final post cure temperature of 325° C. and below, but also resulted in polymer networks with softening temperatures that exceeded the final post cure temperature of the network. Stated a different way, phthalonitrile resin systems that utilize a monofunctional phthalonitrile-allyl diluent and are post cured at the same temperature that will cure the multifunctional phthalonitrile resin in the absence of the diluent (i.e., a final post cure temperature that exceeds the characteristic mechanical tan d peak temperature of the network) attained a network softening temperature (i.e., E'(onset) temperature) that exceeded the final post cure temperature. This feature of the phthalonitrile-allyl diluents enables the design of higher softening temperature phthalonitrile polymerized networks without increasing the final post cure temperature of the network. Thus, phthalonitrile resin systems which employ a reactive diluent and produce networks with softening temperatures greater than 300° C. can be designed that do not require the long time post cure temperatures required of previous high softening temperature multifunctional phthalonitrile resins, post cure temperatures that lead to premature degradation of the polymer during the post cure.

Monofunctional phthalonitrile-allyl diluents are compared to the monofunctional phthalonitrile diluents that lack an allyl moiety. The monofunctional phthalonitriles that lack the allyl functionality are unable to participate in a secondary polymerization mechanism. These diluents tend to lower the softening temperature and alter the mechanical properties (i.e., stiffness, strength, toughness, adhesion) of the network. These attributes can be beneficial for mediating vitrification in a multifunctional phthalonitrile resin that requires extreme temperature post cures during polymerization due to formation of a high softening temperature polymer network (e.g., resorcinol diphthalonitrile ether (RPN)) and improving the stress response of a network when strained.

When adding monofunctional phthalonitrile diluents to multifunctional phthalonitrile resins and resin blends, it is preferred that the molar ratio of the multifunctional phthalonitrile resin (or resin blend) to the monofunctional phthalonitrile be approaching unity, or greater. A ratio at or greater than unity lessens the likelihood of free lower molecular weight polymerized oligomers in the polymer network. Resin formulations with phthalonitrile equivalents of multifunctional phthalonitrile to monofunctional phthalonitrile of much less than unity may suffer from a greater tendency to off gas during cure and greater measurable weight loss at a similar temperature. In certain embodiments, a molar ratio of (e.g., at least one) diphthalonitrile resin to (e.g., at least one) diluent comprises 0.95 or greater, 0.97 or greater, 0.99 or greater, 1.0 or greater, 1.5 or greater, 2 or greater, 5 or greater, 10 or greater, 15 or greater, 20 or greater, 25 or greater, or even 30 or greater; and 50 or less, 45 or less, 40 or less, 35 or less, 32 or less, 27 or less, 23 or less, 19 or less, 14 or less, 9 or less, or even 4 or less. Stated another way, in some embodiments the molar ratio of diphthalonitrile resin to diluent comprises for example 0.95 to 50, inclusive; 0.95 to 9, inclusive; 1.0 to 50, inclusive; 5 to 50, inclusive; or 1.5 to 14, inclusive In certain embodiments, resin blends according to the present disclosure comprise at least one more resin comprising at least one phthalonitrile, in addition to the (e.g., first) diphthalonitrile resin. Example resins comprising at least one phthalonitrile include for instance and without limitation bis(3,4-dicyanophenyl) ether of bisphenol A, bis (2,3-dicyanophenyl) ether of bisphenol A, bis(3,4-dicyanophenyl) ether of bisphenol AP, bis(3,4-dicyanophenyl) ether of bisphenol AF, bis(3,4-dicyanophenyl) ether of bisphenol B, bis(3,4-dicyanophenyl) ether of bisphenol BP, bis(3,4-dicyanophenyl) ether of bisphenol C, bis(3,4-dicyanophenyl) ether of bisphenol C2, bis(3,4-dicyanophenyl) ether of bisphenol E, bis(3,4-dicyanophenyl) ether of bisphenol F, bis(3,4-dicyanophenyl) ether of 3,3',5,5'-tetramethylbisphenol F, bis(3,4-dicyanophenyl) ether of bisphenol FL, bis(3, 4-dicyanophenyl) ether of bisphenol G, bis(3,4-dicyanophenyl) ether of bisphenol M, bis(3,4-dicyanophenyl) ether of bisphenol P, bis(3,4-dicyanophenyl) ether of bisphenol PH, bis(3,4-dicyanophenyl) ether of bisphenol S, bis(3,4-dicyanophenyl) ether of bisphenol T, bis(3,4-dicyanophenyl) ether of bisphenol TMC, bis(3,4-dicyanophenyl) ether of bisphenol Z, bis(3,4-dicyanophenyl) ether of 4,4'-dihydroxybiphenyl, bis(3,4-dicyanophenyl) ether of 4,4'-dihydroxydiphenyl ether, bis(3,4-dicyanophenyl) ether of catechol, bis(3,4-dicyanophenyl) ether of 4,4'-dihydroxybenzophenone, 3,4-dicyanophenyl ether of phenol, 2,3-dicyanophenyl ether of phenol, 4-tert-butylphthalonitrile, 4-butoxyphthalonitrile, 3,4-dicyanophenyl ether of 4-cumylphenol, 3,4-dicyanophenyl ether of 2-allylphenol, and 3,4-dicyanophenyl ether of eugenol. Typically, the resin blend is a solid at 25° C.

The at least one diphthalonitrile resin of a resin blend often comprises a diphthalonitrile resin having a melt temperature that is less than 225° C. and more preferably less than 200° C. In certain embodiments, the at least one diphthalonitrile resin of a resin blend comprises a bisphenol M diphthalonitrile ether resin, a bisphenol P diphthalonitrile ether resin, a bisphenol T diphthalonitrile ether resin, or a combination thereof. Synthesis of diphthalonitrile resins such as BMPN, BPPN, and BTPN can be achieved by the nucleophilic substitution of the nitro group of 4-nitrophthalonitrile by phenolic residues of the bisphenols catalyzed by potassium carbonate in DMSO. The reactions can be conducted at ambient temperature under a nitrogen atmosphere.

Solvents can be used as a processing aid with resin blends according to at least certain embodiments of the present disclosure. Useful solvents are ketones such as acetone, methyl ethyl ketone, methyl isobutyl ketone, cyclopentanone and cyclohexanone; amides such as acetamide, formamide, N,N-dimethylformamide, N-methylpyrrolidinone; sulfones such as tetramethylene sulfone, 3-methylsulfolane, 2,4-dimethylsulfolane, butadiene sulfone, methyl sulfone, ethyl sulfone, propyl sulfone, butyl sulfone, methyl vinyl sulfone, 2-(methylsulfonyl)ethanol, 2,2'-sulfonyldiethanol; sulfoxides such as dimethyl sulfoxide; cyclic carbonates such as propylene carbonate, ethylene carbonate and vinylene carbonate; carboxylic acid esters such as ethyl acetate, methyl cellosolve acetate, methyl formate; and other solvents such as tetrahydrofuran, methylene chloride, dichloromethane, chloroform, acetonitrile, nitromethane, glycol sulfite and 1,2-dimethoxyethane (glyme).

In some embodiments, the resin blend is subjected to a temperature of no more than 300 degrees Celsius in air. Optionally, the resin blend is subjected to a temperature of no more than 300 degrees Celsius at ambient pressure.

In certain embodiments, the resin blend further comprises one or more fillers, for instance at least one of reinforcing continuous fibers or reinforcing discontinuous fibers, a nanofiller, a microfiller, or a combination thereof. Typical compounding techniques utilized to incorporate at least one filler include impellar mixing, high shear mixing, milling, centrifugal mixing, and solution dispersion of particles into the resin blend.

In certain embodiments, the filler comprises a nanofiller comprising metal carbide nanoparticles, metal oxide nanoparticles, silica nanoparticles, carbon nanoparticles, metal carbonate nanoparticles, metal nitride nanoparticles, metal hydroxide nanoparticles, metal sulfate nanoparticles, barium titanate nanoparticles, or a combination thereof. Optionally, the filler comprises a nanofiller comprising calcite nanoparticles, silica nanoparticles, silicon carbide nanoparticles, alumina nanoparticles, zirconia nanoparticles, magnesium oxide nanoparticles, aluminum nitride nanoparticles, boron nitride nanoparticles, dolomite nanoparticles, boehmite nanoparticles, magnesium hydroxide nanoparticles, calcium sulfate nanoparticles, barium sulfate nanoparticles, magnesium sulfate nanoparticles, or a combination thereof. As used herein, the term "nano" or "micro" in front of a material is interchangeable with reference of that material as a nanoparticle or microparticle, respectively (e.g., "nanosilica" is interchangeable with "silica nanoparticles", "microcalcite" is interchangeable with "calcite microparticles", etc.). For instance and without limitation, some suitable nanoparticles include silica nanoparticles available from Nalco Company (Naperville, Ill.) under the trade designation NALCO 15827; and silicon carbide nanoparticles available from 3M Technical Ceramics (Kempten, Germany) under the trade designation VSN 1393.

Typically, a nanofiller is present in resin blends according to the present disclosure in an amount of 1 weight percent or more, 3 weight percent or more, 5 weight percent or more, 8 weight percent or more, 10 weight percent or more, 12 weight percent or more, 15 weight percent or more, 20 weight percent or more, or even 25 weight percent or more, based on the total weight of the resin blend; and 40 weight percent or less, 38 weight percent or less, 36 weight percent or less, 34 weight percent or less, 32 weight percent or less, 30 weight percent or less, 28 weight percent or less, 26 weight percent or less, 24 weight percent or less, 22 weight percent or less, 20 weight percent or less, 18 weight percent or less, or 15 weight percent or less, based on the total weight of the resin blend. Stated another way, a nanofiller may be present in a resin blend in an amount of 1 to 40 weight percent, 1 to 20 weight percent, 3 to 15 weight percent, 20 to 40 weight percent, or 25 to 40 weight percent, based on the total weight of the resin blend.

In certain embodiments, the filler comprises a microfiller comprising metal carbide microparticles, metal oxide microparticles, silica microparticles, carbon microparticles, metal carbonate microparticles, metal nitride microparticles, metal hydroxide nanoparticles, metal sulfate microparticles, barium titanate microparticles, cenospheres, or a combination thereof. Optionally, the filler comprises a microfiller comprising calcite microparticles, silica microparticles, silicon carbide microparticles, alumina microparticles, magnesium oxide microparticles, aluminum nitride microparticles, boron nitride microparticles, dolomite microparticles, boehmite microparticles, glass bubbles, or a combination thereof. For instance and without limitation, some suitable microparticles include boron nitride microparticles available from 3M Company (St. Paul, Minn.) under the trade designation 3M BORON NITRIDE COOLING FILLER PLATELETS; glass bubbles available from 3M Company (St. Paul, Minn.) under the trade designation 3M GLASS BUBBLES IM16K; and alumina microparticles available from Micron Corp (a subsidiary of the Nippon Steel and Sumikin Materials Co., Japan) under the trade designation MICRON TA6Y1 ALUMINA.

Typically, a microfiller is present in resin blends according to the present disclosure in an amount of 1 weight percent or more, 5 weight percent or more, 10 weight percent or more, 15 weight percent or more, 20 weight percent or more, 30 weight percent or more, 40 weight percent or more, 50 weight percent or more, or even 60 weight percent or more, based on the total weight of the resin blend; and 90 weight percent or less, 85 weight percent or less, 80 weight percent or less, 75 weight percent or less, 70 weight percent or less, 65 weight percent or less, 55 weight percent or less, 45 weight percent or less, 35 weight percent or less, or 25 weight percent or less, based on the total weight of the resin blend. Stated another way, a microfiller may be present in a resin blend in an amount of 1 to 90 weight percent, 1 to 50 weight percent, 5 to 35 weight percent, 20 to 55 weight percent, or 60 to 90 weight percent, based on the total weight of the resin blend.

Generally, the optional surface modifiers of the present disclosure include at least a binding group and a compatibilizing segment. The compatiblizing segment is selected to improve the compatibility of filler with the curable resin. Generally, the selection of the compatibilizing group depends on a number of factors including the nature of the curable resin, the concentration of the filler, and the desired degree of compatibility. Useful compatibilizing groups include for instance and without limitation, polyalkylene oxide residues (e.g., polypropylene oxide, polyethylene oxide, and combinations thereof), aromatic residues (e.g., phenyl, phenylalkylene, substituted phenylene, and combinations thereof), carbonyl residues (e.g., ketone, ester, amide, carbamate, and combinations thereof). The binding group bonds to the particle surface, connecting the surface-modifying agent to the filler. In the case of calcite particles, unlike many silica-based nanoparticle systems wherein the surface-modifying agents are covalently bonded to the silica, the surface-modifying agents of the present disclosure are ionically bonded to or physically bonded to (e.g., associated with) the calcite particles. Depending on the filler surface and the surface modifier, the surface modifier may be one or more of covalently bonded, ionically bonded, or physically bonded to a surface of the filler.

Some suitable surface modifiers comprise an organoacid, an organobase, a siloxane, a silane, or a combination thereof. The type of surface modifier will depend on the material of the filler. For instance, the surface modifier may comprise a silane or a siloxane when the filler comprises silica nanoparticles, silica microparticles, cenospheres, zirconia nanoparticles, zirconia microparticles, magnesium oxide nanoparticles, magnesium oxide microparticles, silicon carbide nanoparticles, silicon carbide microparticles, or a combination thereof. The surface modifier may comprise an organoacid or an organobase when the filler comprises calcite nanoparticles, calcite microparticles, magnesium oxide nanoparticles, magnesium oxide microparticles, alumina nanoparticles, alumina microparticles, dolomite nanoparticles, dolomite microparticles, boehmite nanoparticles, boehmite microparticles, or a combination thereof. The surface modifier may comprise an organoacid when the filler comprises zirconia nanoparticles, zirconia microparticles, magnesium oxide nanoparticles, magnesium oxide microparticles, or a combination thereof. The surface modifier may comprise an organosulfonate and/or an organophosphate when the filler comprises calcite nanoparticles, calcite microparticles, or a combination thereof. For example, the sulfonate and phosphate ends of organosulfonates and organophosphates, respectively, associate with the calcite surface by the formation of an ionic complex between sulfonate and phosphate of the surface modifier and calcium of the calcite. The organic end of the surface modifier stabilizes the calcite in the phthalonitrile resin, resulting in a calcite dispersion in the liquid resin melt and stabilized calcite in the cured polymer network. At least certain embodiments of the present disclosure utilize polypropylene oxide and polyethylene oxide as the organic end of any of the surface modifiers described herein, associated with the monomer resin and polymer network.

For instance, according to the present disclosure, a phenylsilane surface modified nanosilica sol was blended with a phthalonitrile resin blend incorporating 4-(2-allylphenoxy) phthalonitrile reactive diluent and solvent stripped. The phenylsilane modified surface compatibilizes the silica nanoparticles with the phthalonitrile resin. Alumina, boron nitride, and glass bubbles were previously centrifugally mixed into the a phthalonitrile resin blend incorporating 4-(2-allylphenoxy)phthalonitrile reactive diluent, as described in co-owned Application Ser. No. 62/475,396. The reactive diluent lowers the resin viscosity, enabling effective dispersion and higher loading of particles at lower temperatures. Calcite and a surface modifier may be impeller mixed and milled into a phthalonitrile resin blend with a reactive diluent at lower temperatures than without the diluent. The surface modifier absorbs to the calcite surface and stabilizes the calcite in the resin. The filled resins maintain a working time comparable to the unfilled resin when a curative or catalyst is added.

Impeller mixing and milling as a compounding technique for a calcite filled phthalonitrile resin blend provides process simplicity, ease, and low cost compared to other compounding techniques. Impellar mixing disperses the calcite in the resin and breaks the particle size down to micrometer particle diameters. Milling as a follow-on process breaks the calcite down to nanometer particle diameters, while the surface modifier stabilizes the calcite in the resin. Impellar mixing plus milling enables the low cost of the filler to be effectively transferred to the cost of the filled resin. For instance, a BMPN resin and BMPN based phthalonitrile blend with a reactive diluent would enable mixing and milling as compounding techniques where previous phthalonitrile resins do not, by maintaining a liquid state at temperatures below 150 degrees Celsius.

At temperatures near to 60 degrees Celsius, solvent is often added to reduce the viscosity of the resin. Some suitable solvents miscible with phthalonitrile resins include methyl ethyl ketone (MEK), methyl isobutyl ketone (MIBK), diacetone alcohol, dimethylformamide (DMF), and dimethyl sulfoxide (DMSO). At higher temperatures (e.g., greater than 120 degrees Celsius but less than 200 degrees Celsius), mixing and milling can be performed without the addition of solvent in a liquid resin melt. An advantage of high temperature mixing and milling is the removal of solvent stripping.

A surface modifying agent for a filler surface is selected such that one end of the surface modifier preferentially associates with the filler surface and the other end of the surface modifier preferentially associates with the monomer resin and maintains particle compatibility in the resin and polymerized network. The concentration of a surface modifier can be tuned to minimize free surface modifier in the resin and avoid open filler (e.g., calcite) surface, both of which would catalyze phthalonitrile polymerization over 200 degrees Celsius.

In certain embodiments, the filler comprises at least one of reinforcing continuous fibers or reinforcing discontinuous fibers. Exemplary fibers include carbon (e.g., graphite) fibers, glass fibers, ceramic fibers, boron fibers, silicon carbide fibers, polypropylene fibers, polyacrylonitrile fibers, polyimide fibers, polyamide fibers, and polyethylene fibers. Combinations of materials may also be used. Generally, the form of the fibers is not particularly limited. Exemplary continuous fiber forms include unidirectional arrays of individual continuous fibers, yarn, roving, braided, and nonwoven mats. Discontinuous fibers are not particularly limited, and for example include inorganic fibers, such as glass, alumina, aluminosilicate, carbon, basalt, or a combination thereof. The discontinuous fibers typically have an average length of less than 5 centimeters. Discontinuous fibers may be formed from continuous fibers, for example, by methods known in the art such as chopping, shearing, and milling. Typically, the plurality of discontinuous fibers comprises an aspect ratio of 10:1 or greater.

Suitable discontinuous fibers can have a variety of compositions, such as ceramic fibers. The ceramic fibers can be produced from a variety of commercially available ceramic filaments. Examples of filaments useful in forming the ceramic fibers include the ceramic oxide fibers sold under the trademark NEXTEL (3M Company, St. Paul, Minn.). NEXTEL is a continuous filament ceramic oxide fiber having low elongation and shrinkage at operating temperatures, and offers good chemical resistance, low thermal conductivity, thermal shock resistance, and low porosity. Specific examples of NEXTEL fibers include NEXTEL 312, NEXTEL 440, NEXTEL 550, NEXTEL 610 and NEXTEL 720. NEXTEL 312 and NEXTEL 440 are refractory aluminoborosilicate that includes $Al_2O_3$, $SiO_2$ and $B_2O_3$. NEXTEL 550 and NEXTEL 720 are aluminosilica and NEXTEL 610 is alumina. During manufacture, the NEXTEL filaments are coated with organic sizings or finishes which serve as aids in textile processing. The sizing can be removed from the ceramic filaments by heat cleaning the filaments or ceramic fibers as a temperature of 700° C. for one to four hours. Boron nitride fibers can be made, for example, as described in U.S. Pat. No. 3,429,722 (Economy) and U.S. Pat. No. 5,780,154 (Okano et al.).

Ceramic fibers can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers which contain less than about 2% alkali or are substantially free of alkali (i.e., "E-glass" fibers). E-glass fibers are available from numerous commercial suppliers.

The ceramic fibers can be cut or chopped so as to provide relatively uniform lengths, which can be accomplished by cutting continuous filaments of the ceramic material in a mechanical shearing operation or laser cutting operation, among other cutting operations. Given the highly controlled nature of such cutting operations, the size distribution of the ceramic fibers is very narrow and allow to control the composite property. The length of the ceramic fiber can be determined, for instance, using an optical microscope (Olympus MX61, Tokyo, Japan) fit with a CCD Camera (Olympus DP72, Tokyo, Japan) and analytic software (Olympus Stream Essentials, Tokyo, Japan). Samples may be prepared by spreading representative samplings of the ceramic fiber on a glass slide and measuring the lengths of at least 200 ceramic fibers at 10× magnification.

The amount of discontinuous fibers dispersed in the resin blend is not particularly limited. The plurality of fibers is often present in an amount of at least 1 weight percent of the resin blend, at least 2 weight percent, at least 3 weight percent, at least 5 weight percent, at least 10 weight percent, at least 15 weight percent, at least 20 weight percent, or at least 25 weight percent of the resin blend; and up to 50 weight percent, up to 45 weight percent, up to 40 weight percent, or up to 35 weight percent of the resin blend. In certain embodiments, the fibers are present in the resin blend in an amount of between 1 weight percent and 50 weight percent, or between 2 weight percent and 25 weight percent, or between 5 weight percent and 15 weight percent, inclusive, of the resin blend. In certain embodiments, discontinuous fibers are present in an amount of between 5 weight percent and 50 weight percent, inclusive, of the resin blend.

For example, a calcite filled BMPN based resin system produced by impeller mixing of calcite and a surface modifier, and followed by milling of the calcite to dimensions of less than 400 nm, has been employed previously in the fabrication of a fiber reinforced polymer composite, as described in co-owned Application Ser. No. 62/475,396. The nanometer dimension of the particles enables penetration of the resin and particle into the fiber bundles (without filtering of the particles).

The low viscosity of the phthalonitrile blends with reactive diluents resin system enables impregnation of the fiber at temperatures below 100 degrees Celsius. The present disclosure also describes resin transfer molding as a manufacturing method for liquid phthalonitrile resin impregnation of fiber in the production of a fiber reinforced polymer composite. Other in-line liquid resin impregnation methods of fibers enabled by phthalonitrile blends with reactive diluents include pultrusion and filament winding. A fiber reinforced polymer composite has been demonstrated with a phthalonitrile blend with a reactive diluent resin system using a resin transfer molding process similar to a process that may be employed for a calcite filled, silica filled or silicon carbide filled phthalonitrile resin system.

Solution dispersion followed by solvent stripping can be a preferred method for the introduction of silica into the resin blends. The solution dispersion method for silica is low cost compared to the expense of the phthalonitrile resin and yields well dispersed particles in the liquid resin melt at temperatures below 200 degrees Celsius, even below 120 degrees Celsius. For example, the silica was surface modified with phenyltrimethoxysilane in a water/alcohol suspension and transferred to a solvent (e.g., methoxypropanol, butyl acetate, acetone, MEK, MIBK, tetrahydrofuran (THF), dichloromethane, diacetone alcohol, DMF, DMSO) miscible with phthalonitrile resins. The particle sol was added at elevated temperature (e.g., 90 degrees Celsius) to the undiluted phthalonitrile resin where the resin is a low viscosity liquid resin melt. The particle sol can be added at lower temperatures (e.g., less than 90 degrees Celsius) to the resin blend diluted with a miscible solvent to lower the resin viscosity. Solvent is stripped from the particle filled resin at temperatures less than 150 degrees Celsius, where the resin blend remains in a liquid melt state. The phenyl treated surface of the particle stabilizes the particles in the liquid resin melt and in the cured polymer network.

Centrifugal mixing of alumina, boron nitride, glass bubbles and silane surface modified glass bubbles offers a short time and efficient means of particle dispersion in a phthalonitrile blend with a reactive diluent, as described in co-owned Application Ser. No. 62/475,396. Particles are dispersed in the liquid resin at a temperature below 200 degrees Celsius, preferably between 100 to 150 degrees Celsius, where the resin viscosity and RPM of the centrifugal mixer yield well mixed particles with no visual agglomerates on the order of minutes.

Particle filled phthalonitrile resin blends with reactive diluents can be processable as a liquid melt at temperatures below 200 degrees Celsius, even below 150 degrees Celsius. The diluent lowers the viscosity of the resin at a set temperature, which improves the dispersion of the particles by centrifugal mixing and enables higher particle loading.

The manufacture of fiber reinforced polymer fibrous composite articles from a filled resin is enabled by the characteristic size of a particle filler mapped to a sphere being less than 1 micrometer, more preferably less than 400 nanometers, such as for solution dispersed silica and potentially milled calcite and solution dispersed silicon carbide filled phthalonitrile resins.

Resin blends according to at least certain embodiments of the disclosure include one or more curatives. Such curatives often include an amine compound, such as a primary amine, for instance including an aniline functional residue. Combinations of various curatives can be used if desired. If present, the curative is typically present in an amount of at least 1 percent by weight of the resin blend, at least 2 percent, at least 5 percent, at least 10 percent, at least 15 percent or even at least 20 percent by weight of the resin blend; and up to 40 percent by weight of the resin blend, up to 35 percent, up to 30 percent, or even up to 25 percent by weight of the resin blend; such as between 0 and 40 percent by weight of the resin blend. Higher molecular weight and lower volatility aniline functional curatives are typically desired to avoid loss of the curative during polymerization. Dianiline based curatives can be of value due to a higher aniline functionality per weight of the curative. Example dianiline based curatives that will promote phthalonitrile polymerization include for instance and without limitation, 4,4'-(1,3-phenylenedioxy)dianiline, 4,4'-(1,4-phenylenedioxy)dianiline, bis[4-(4-aminophenoxy)phenyl]sulfone, 4,4'-(4,4'-isopropylidenediphenyl-1,1'-diyldioxy)dianiline, 4,4'-(1,3-phenylenediisopropylidene)dianiline, 4,4'-(1,4-phenylenediisopropylidene)dianiline, 4,4'-(1,1'-biphenyl-4,4'-diyldioxy)dianiline, 4,4'-methylenedianiline, 4,4'-sulphonyldianiline, 4,4'-methylene-bis(2-methylaniline), 3,3'-methylenedianiline, 3,4'-methylenedianiline, 4,4'-oxydianiline, 4,4'-(isopropylidene)dianiline, 4,4'-(hexafluoroisopropylidene)dianiline, 4,4'-(hexafluoroisopropylidene)bis(p-phenyleneoxy)dianiline, and 4,4'-diaminobenzophenone. The primary amine promoted phthalonitrile cure reaction proceeds at an appreciable rate between temperatures of 200° C. to 250° C. Amine cured phthalonitrile polymerized networks have demonstrated excellent thermal stability imparted by a high glass transition temperature, good thermal and thermoxidative degradation resistance, plus are inherently non-flammable, and have low moisture uptake.

Certain other optional additives may also be included in resin blends according to the present disclosure, including, for example, tougheners, fillers, and combinations thereof. Such additives provide various functions. For instance, a toughening agent such as organic particles, may add strength to the composition after curing without interfering with curing. It will be understood by one of skill in the art that one compound may form two or more different functions. For example, a compound may function as both a toughening agent and a filler. In some embodiments, such additives will not react with the resins of the resin blend. In some embodiments, such additives may include reactive functional groups, particularly as end groups. Examples of such reactive functional groups include, but are not limited to, amines, thiols, alcohols, epoxides, vinyls, and combinations thereof.

Useful toughening agents are polymeric compounds having both a rubbery phase and a thermoplastic phase such as: graft polymers having a polymerized, diene, rubbery core and a polyacrylate, polymethacrylate shell; graft polymers having a rubbery, polyacrylate core with a polyacrylate or polymethacrylate shell; and elastomeric particles polymerized in situ in the epoxide from free radical polymerizable monomers and a copolymerizable polymeric stabilizer.

Examples of useful toughening agents of the first type include graft copolymers having a polymerized, diene, rubbery backbone or core to which is grafted a shell of an acrylic acid ester or methacrylic acid ester, monovinyl aromatic hydrocarbon, or a mixture thereof, such as disclosed in U.S. Pat. No. 3,496,250 (Czerwinski). Exemplary rubbery backbones include polymerized butadiene or a polymerized mixture of butadiene and styrene. Exemplary shells including polymerized methacrylic acid esters are lower alkyl ($C_1$-$C_4$) substituted methacrylates. Exemplary monovinyl aromatic hydrocarbons are styrene, alpha-methylstyrene, vinyltoluene, vinylxylene, ethylvinylbenzene, isopropylstyrene, chlorostyrene, dichlorostyrene, and ethylchlorostyrene. It is important that the graft copolymer contain no functional groups that would interfere with the polymerization of the resin.

Examples of useful toughening agents of the second type are acrylate core-shell graft copolymers wherein the core or backbone is a polyacrylate polymer having a glass transition temperature below 0° C., such as polybutyl acrylate or polyisooctyl acrylate to which is grafted a polymethacrylate polymer (shell) having a glass transition above 25° C., such as polymethylmethacrylate.

The third class of useful toughening agents includes elastomeric particles that have a glass transition temperature ($T_g$) below 25° C. before mixing with the other components of the composition. These elastomeric particles are polymerized from free radical polymerizable monomers and a copolymerizable polymeric stabilizer. The free radical polymerizable monomers are ethylenically unsaturated monomers or diisocyanates combined with co-reactive difunctional hydrogen compounds such as diols, diamines, and alkanolamines.

Useful toughening agents include core/shell polymers, such as methacrylate-butadiene-styrene (MBS) copolymer wherein the core is crosslinked styrene/butadiene rubber and the shell is polymethylacrylate (for example, those available under the trade names ACRYLOID KM653 and KM680, from Rohm and Haas, Philadelphia, Pa.), those having a core including polybutadiene and a shell including poly(methyl methacrylate) (for example, those available under the trade names KANE ACE M511, M521, B11A, B22, B31, and M901 from Kaneka Corporation, Houston, Tex. and CLEARSTRENGTH C223 from ATOFINA, Philadelphia, Pa.), those having a polysiloxane core and a polyacrylate shell (for example, those available under the trade names CLEARSTRENGTH S-2001 from ATOFINA and GENIOPERL P22 from Wacker-Chemie GmbH, Wacker Silicones, Munich, Germany), those having a polyacrylate core and a poly(methyl methacrylate) shell (for example, those available under the trade names PARALOID EXL2330 from Rohm and Haas and STAPHYLOID AC3355 and AC3395 from Takeda Chemical Company, Osaka, Japan), those having an MBS core and a poly(methyl methacrylate) shell (for example, those available under the trade names PARALOID EXL2691A, EXL2691, and EXL2655 from Rohm and Haas); and the like; and mixtures thereof.

As used above, for acrylic core/shell materials "core" will be understood to be an acrylic polymer having a $T_g$ of less than 0° C. and "shell" will be understood to be an acrylic polymer having a $T_g$ of greater than 25° C.

Other useful toughening agents include: carboxylated and amine terminated acrylonitrile/butadiene vulcanizable elastomer precursors, such as those available under the trade names HYCAR CTBN 1300X8, ATBN 1300X16, and HYCAR 1072 from B. F. Goodrich Chemical Co.; butadiene polymers, such as those available under the trade name HYCAR CTB; amine functional polyethers such as HCl 101 (i.e., polytetramethylene oxide diamine) a 10,000 MW, primary amine-terminated, compound from 3M Co., St. Paul, Minn., and those available under the trade name JEFFAMINE from Huntsman Chemical Co., Houston, Tex. Useful liquid poly-butadiene hydroxyl terminated resins include those available under the trade names LIQUIFLEX H by Petroflex of Wilmington, Del., and HT 45 by Sartomer of Exton, Pa.

Tougheners may include epoxy-terminated compounds, which can be incorporated into the polymer backbone. A typical, preferred, list of tougheners includes: acrylic core/shell polymers; styrene-butadiene/methacrylate core/shell polymers; polyether polymers; carboxylated acrylonitrile/butadienes; and carboxylated butadienes. Advantages can be obtained from the provision of the chain extension agent in a composition with an epoxy resin even in the absence of a toughening agent as described above. However, particular advantage is achieved from the presence of the toughening agent or combinations of different agents, as previously suggested.

Various combinations of toughening agents can be used if desired. If used, a toughening agent is present in the resin blend in an amount of at least 3 percent by weight, or at least 5 percent by weight. If used, a toughening agent is present in a resin blend in an amount of no greater than 35 percent by weight, or no greater than 25 weight percent.

Other optional additives, or adjuvants, may be added to the compositions as desired. Examples of such other optional additives include as colorants, anti-oxidant stabilizers, thermal degradation stabilizers, light stabilizers, flow agents, bodying agents, flatting agents, additional fillers, binders, blowing agents, fungicides, bactericides, surfactants, plasticizers, rubber tougheners, and other additives known to those skilled in the art. Such additives are typically substantially unreactive. These adjuvants, if present, or other optional additives, are added in an amount effective for their intended purpose.

Examples of additional suitable filler materials include reinforcement-grade carbon black, fluoroplastics, clays, and any combination of any of these in any proportions.

The phrase "reinforcement-grade carbon black" as used herein, includes any carbon black with an average particle size smaller than about 10 microns. Some particularly suitable average particle sizes for reinforcement-grade carbon black range from about 9 nm to about 40 nm. Carbon black that is not reinforcement grade include carbon black with an average particle size larger than about 40 nm. Carbon nanotubes are also useful fillers. Carbon black fillers are typically employed as a means to balance, elongation, hardness, abrasion resistance, conductivity, and processibility of compositions. Suitable examples include MT blacks (medium thermal black) designated N-991, N-990, N-908, and N-907; FEF N-550; and large particle size furnace blacks.

Further useful fillers include diatomaceous earth, barium sulfate, talc, and calcium fluoride. The choice and amounts of optional components depend on the needs of the specific application.

Advantageously, resin blends according to the present disclosure are suitable for use in a prepreg, which includes any reinforcing or molding material that can be impregnated with the resin blend. Hence, in a second aspect, a prepreg is provided comprising continuous reinforcing fibers and a resin blend impregnated into the continuous reinforcing fibers. In a third aspect, another prepreg is provided comprising a cloth and a resin blend impregnated into the cloth. Similarly, in a fourth aspect, a molding compound is provided. The molding compound includes chopped reinforcing fibers distributed in the resin blend. The resin blend of each of the second aspect, the third aspect, and the fourth aspect is in accordance with the first aspect described in detail above. The resin blends of the disclosure can be used to make composite articles by a variety of conventional processes, e.g., resin transfer molding, filament winding, tow placement, resin infusion processes, compression molding, or traditional prepreg processes. Prepregs can be prepared by impregnating an array of fibers (or a fabric) with the resin blend and then layering the impregnated tape or fabric. The resulting prepreg can then be cured by application of heat, along with the application of pressure or vacuum (or both) to remove any trapped air.

In a fifth aspect, an article is provided. The article includes a polymerization product of the resin blend according to the first aspect. A method of making a polymerization product typically includes obtaining at least one diluent comprising a single phthalonitrile functional group, blending the (at least one) diluent with at least one diphthalonitrile resin, a curative, a catalyst (e.g., a base such as 1,5-diazabicyclo (4.3.0)non-5-ene or 1,8-diazabicyclo[5.4.0]undec-7-ene; reducing agents such as hydroquinone and 1,2,3,6-tetrahydropyridine; metal, organometals or metal salts such as copper, iron, copper acetylacetonate, zinc naphthenate, dibutyltin dilaurate, stannous chloride, stannic chloride, copper chloride, iron chloride, and/or calcium carbonate), or a combination thereof to form a resin blend; and subjecting the resin blend to an elevated temperature to form a fully polymerized network. Generally, the composition is heated to a temperature between about 50° C. and 300° C., such as between about 130-300° C., for a time of about 1-480 minutes. Suitable sources of heat include induction heating coils, ovens, hot plates, heat guns, infrared sources including lasers, microwave sources.

Figure 3:
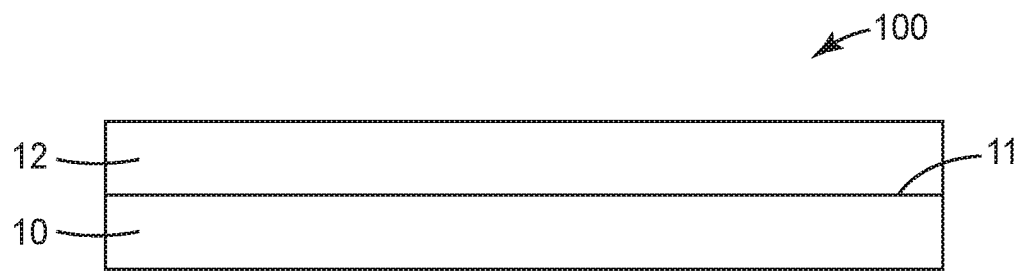
FIG. 3 is a schematic cross-sectional view of an exemplary article according to the present disclosure.

In a sixth aspect, another article is provided. The article includes a substrate and a layer of the resin blend disposed on the substrate. The resin blend is in accordance with the first aspect described in detail above. Referring to FIG. 3, a schematic cross-sectional view is provided of an exemplary article 100 comprising a substrate 10 having a first major surface 11 and a layer of a resin blend 12 disposed on (e.g., adhered to) the first major surface 11 of the substrate 10. The layer of the resin blend 12 covers at least a portion of the first major surface 11 of the substrate 10.

The thickness of the layer of the resin blend is not particularly limited, and can comprise a thickness of 15 micrometers (m) or greater, 20 µm or greater, 25 µm or greater, 30 µm or greater, 50 µm or greater, 75 µm or greater, 100 µm or greater, 125 µm or greater, or even 150 µm or greater; and 300 µm or less, 275 µm or less, 250 µm or less, 225 µm or less, 200 µm or less, or even 175 µm or less.

The article is typically an adhesive article, suitable for adhering at least one substrate to another substrate or material. The substrate of the article is not limited, and can comprise for instance and without limitation, paper, polymeric film, glass, ceramic, wood, metal, fiber reinforced polymeric material, woven cloth, non-woven matrix, or a combination thereof. In some favored embodiments, the substrate comprises a release liner. The release liner can be of a variety of forms including, e.g., sheet, web, tape, and film. Examples of suitable materials include, e.g., paper (e.g., kraft paper, poly-coated paper and the like), polymer films (e.g., polyethylene, polypropylene and polyester), composite liners, and combinations thereof. Release liners can optionally include a variety of markings and indicia including, e.g., lines, art work, brand indicia, and other information. One example of a useful release liner is a fluoroalkyl silicone polycoated paper.

Exemplary Embodiments of the Disclosure

Embodiment 1 is a resin blend. The resin blend includes at least one diluent comprising a single phthalonitrile functional group and at least one diphthalonitrile resin. The at least one diluent comprises a compound of formula I:

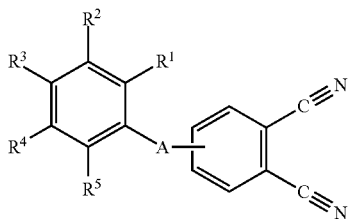

wherein $R^1$, $R^2$, $R^3$, $R^4$, and $R^5$ are independently selected from H, an allyl group, a $C_1$ to $C_{20}$ alkyl group, an aryl group, an ether group, a thioether group, an aldehyde group, a ketone group, an ester group, an amide group, an acid group, a sulfonyl, a halogen, a nitro, a cyano, a secondary amine group, a tertiary amine group, or a combination thereof, and wherein A is oxygen or sulfur.

Embodiment 2 is the resin blend of embodiment 1, wherein the at least one diluent comprises a compound of formula II:

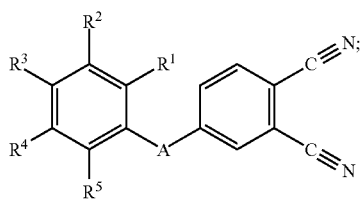

wherein $R^1$, $R^2$, $R^3$, $R^4$, $R^5$, and A are each as defined with respect to formula I.

Embodiment 3 is the resin blend of embodiment 1 or embodiment 2, wherein one or more of $R^1$, $R^2$, $R^3$, $R^4$, and $R^5$, is an allyl group.

Embodiment 4 is the resin blend of any of embodiments 1 to 3, wherein A is oxygen.

Embodiment 5 is the resin blend of any of embodiments 1 to 4, wherein the at least one diluent includes at least one of 4-(2-methoxy-4-allylphenoxy)phthalonitrile, 4-(2-allylphenoxy)phthalonitrile, 4-(4-tert-butylphenoxy)phthalonitrile, and 4-(3-methylphenoxy)phthalonitrile.

Embodiment 6 is the resin blend of any of embodiments 1 to 5, wherein the at least one diluent includes 4-(2-methoxy-4-allylphenoxy)phthalonitrile.

Embodiment 7 is the resin blend of any of embodiments 1 to 6, wherein the at least one diluent includes 4-(2-allylphenoxy)phthalonitrile.

Embodiment 8 is the resin blend of any of embodiments 1 to 7, wherein the at least one diluent includes 4-(4-tert-butylphenoxy)phthalonitrile.

Embodiment 9 is the resin blend of any of embodiments 1 to 8, wherein the at least one diluent includes 4-(3-methylphenoxy)phthalonitrile.

Embodiment 10 is the resin blend of any of embodiments 1 to 9, wherein a molar ratio of the at least one diphthalonitrile resin to the at least one diluent is 0.95 or greater.

Embodiment 11 is the resin blend of any of embodiments 1 to 10, wherein the molar ratio of the at least one diphthalonitrile resin to the at least one diluent is 1.0 or greater.

Embodiment 12 is the resin blend of any of embodiments 1 to 10, wherein the molar ratio of at least one diphthalonitrile resin to the at least one diluent ranges from 0.95 to 50, inclusive.

Embodiment 13 is the resin blend of any of embodiments 1 to 12, wherein the at least one diphthalonitrile resin includes a bisphenol M diphthalonitrile ether resin, a bisphenol P diphthalonitrile ether resin, a bisphenol T diphthalonitrile ether resin, or a combination thereof.

Embodiment 14 is the resin blend of any of embodiments 1 to 13, wherein the at least one diphthalonitrile resin includes a bisphenol M diphthalonitrile ether resin.

Embodiment 15 is the resin blend of any of embodiments 1 to 14, wherein the at least one diphthalonitrile resin includes a bisphenol P diphthalonitrile ether resin.

Embodiment 16 is the resin blend of any of embodiments 1 to 15, wherein the at least one diphthalonitrile resin includes a bisphenol T diphthalonitrile ether resin.

Embodiment 17 is the resin blend of any of embodiments 1 to 16, further including a resorcinol diphthalonitrile ether resin.

Embodiment 18 is the resin blend of any of embodiments 1 to 17, further including a filler.

Embodiment 19 is the resin blend of embodiment 18, wherein the filler includes at least one of reinforcing continuous fibers or reinforcing discontinuous fibers.

Embodiment 20 is the resin blend of embodiment 18 or embodiment 19, wherein the filler includes a nanofiller comprising metal carbide nanoparticles, metal oxide nanoparticles, silica nanoparticles, carbon nanoparticles, metal carbonate nanoparticles, metal nitride nanoparticles, metal hydroxide nanoparticles, metal sulfate nanoparticles, barium titanate nanoparticles, or a combination thereof.

Embodiment 21 is the resin blend of any of embodiments 18 to 20, wherein the filler includes a nanofiller including calcite nanoparticles, silica nanoparticles, silicon carbide nanoparticles, alumina nanoparticles, zirconia nanoparticles, magnesium oxide nanoparticles, aluminum nitride nanoparticles, boron nitride nanoparticles, dolomite nanoparticles, boehmite nanoparticles, magnesium hydroxide nanoparticles, calcium sulfate nanoparticles, barium sulfate nanoparticles, magnesium sulfate nanoparticles, or a combination thereof.

Embodiment 22 is the rein blend of any of embodiments 18 to 21, wherein the filler includes a microfiller comprising metal carbide microparticles, metal oxide microparticles, silica microparticles, carbon microparticles, metal carbonate microparticles, metal nitride microparticles, metal hydroxide nanoparticles, metal sulfate microparticles, barium titanate microparticles, cenospheres, or a combination thereof.

Embodiment 23 is the resin blend of any of embodiments 18 to 22, wherein the filler includes a microfiller comprising calcite microparticles, silica microparticles, silicon carbide microparticles, alumina microparticles, magnesium oxide microparticles, aluminum nitride microparticles, boron nitride microparticles, dolomite microparticles, boehmite microparticles, glass bubbles, or a combination thereof.

Embodiment 24 is the resin blend of any of embodiments 18 to 23, including a nanofiller in an amount of 1 weight percent to 40 weight percent, inclusive, based on the total weight of the resin blend.

Embodiment 25 is the resin blend of any of embodiments 18 to 23, including a microfiller in an amount of 1 weight percent to 90 weight percent, inclusive, based on the total weight of the resin blend.

Embodiment 26 is the resin blend of any of embodiments 1 to 25, further including at least one additive selected from a catalyst, a curative, a toughening agent, and combinations thereof.

Embodiment 27 is the resin blend of embodiment 26, wherein the curative comprises a primary amine.

Embodiment 28 is the resin blend of embodiment 27, wherein the primary amine curative comprises an aniline functional residue.

Embodiment 29 is the resin blend of any of embodiments 26 to 28, wherein the curative is present in an amount of 0 to 40 weight percent, based on the total weight of the resin blend.

Embodiment 30 is a prepreg. The prepreg includes continuous reinforcing fibers and the resin blend of any of embodiments 1 to 29 impregnated into the continuous reinforcing fibers.

Embodiment 31 is a prepreg. The prepreg includes a cloth and the resin blend of any of embodiments 1 to 29 impregnated into the cloth.

Embodiment 32 is a molding compound. The molding compound includes chopped reinforcing fibers distributed in the resin blend of any of embodiments 1 to 29.

Embodiment 33 is an article. The article includes a polymerization product of the resin blend of any of embodiments 1 to 29.

Embodiment 34 is an article. The article includes a substrate and a layer of the resin blend of any of embodiments 1 to 29 disposed on the substrate.

Embodiment 35 is the article of embodiment 34, wherein the substrate comprises a release liner.

Examples

Materials and Methods

The chemicals used with their sources are shown in Table 1. All materials were obtained from commercial sources and used as received.

TABLE 1

| Raw materials and sources | | |
|---|---|---|
| Abbreviation | Description | Source |
| BMPN | Bisphenol M diphthalonitrile (i.e., bis(3,4-dicyanophenyl) ether of bisphenol M); prepared as described in Preparatory Example A of U.S. patent application No. 62/316,248 fried on 31 Mar. 2016 | |
| RPN | Resorcinol diphthalonitrile (i.e., bis(3,4-dicyanophenyl) ether of resorcinol); prepared as described in Preparatory Example B of U.S. patent application No. 62/316,248 fried on 31 Mar. 2016 | |
| BTPN | Bisphenol T diphthalonitrile (i.e., bis(3,4-dicyanophenyl) ether of bisphenol T); prepared as described in Preparatory Example C of U.S. patent application No. 62/316,248 fried on 31 Mar. 2016 | |
| BPPN | Bisphenol P diphthalonitrile (i.e., bis(3,4-dicyanophenyl) ether of bisphenol P); prepared as described in Preparatory Example D of U.S. patent application No. 62/316,248 filed on 31 Mar. 2016 | |
| APPN | Allylphenol phthalonitrile (i.e., 4-(2-allylphenoxy)phthalonitrile); prepared as described below | |
| EuPN | Eugenol phthalonitrile (i.e., 4-(2-methoxy-4-allylphenoxy)phthalonitrile); prepared as described below | |
| tBPPN | 4-(4-tert-butylphenoxy)phthalonitrile; prepared as described below | |
| mCPN | 4-(3-methylphenoxy)phthalonitrile; prepared as described below | |
| DMSO | Dimethyl sulfoxide; $(CH_3)_2SO$ | Sigma Aldrich Chemical Company, St. Louis, MO |
| Eugenol | $4\text{-}(H_2C\!=\!CHCH_2)C_6H_3\text{-}2\text{-}(OCH_3)OH$ | Sigma Aldrich Chemical Company, St. Louis, MO |
| 2-allylphenol | $H_2C\!=\!CHCH_2C_6H_4OH$ | Sigma Aldrich Chemical Company, St. Louis, MO |
| $K_2CO_3$ | Potassium carbonate | Sigma Aldrich Chemical Company, St. Louis, MO |
| 4,4'-(1,3-phenylenedioxy)dianiline | $C_6H_4(OC_6H_4NH_2)_2$ | Sigma Aldrich Chemical Company, St. Louis, MO |
| 4-nitrophthalonitrile | $O_2NC_6H_3\text{-}1,2\text{-}(CN)_2$ | Sigma Aldrich Chemical Company, St. Louis, MO |

TABLE 1-continued

Raw materials and sources

| Abbreviation | Description | Source |
| --- | --- | --- |
| 4-tert-butylphenol | $(CH_3)_3CC_6H_4OH$ | Sigma Aldrich Chemical Company, St. Louis, MO |
| m-cresol | $CH_3C_6H_4OH$ | Sigma Aldrich Chemical Company, St. Louis, MO |
| trimethoxyphenylsilane | $C_6H_5Si(OCH_3)_3$ | Sigma Aldrich Chemical Company, St. Louis, MO |
| 1-methoxy-2-propanol | $CH_3CH(OH)CH_2OCH_3$ | Sigma Aldrich Chemical Company, St. Louis, MO |
| butyl acetate | $CH_3COO(CH_2)_3CH_3$ | Sigma Aldrich Chemical Company, St. Louis, MO |
| NALCO 15827 | 140 nm diameter silica aqueous sol | Nalco Company, Naperville, IL |

Method for Preparing PS-Nanosilica 249.5 kg of NALCO 15827 was added to a kettle with stirring. A premix of 2.105 kg of trimethoxyphenylsilane in 203.2 kg of 1-methoxy-2-propanol was pumped into the kettle containing the NALCO 15827 and mixed for 30 minutes. The solution was pumped into a hot tube reactor as described in U.S. Pat. No. 8,394,977 with a reaction temperature of 149° C. and pressure of 20.4 atmospheres (2.07 MPa). The mixture was held at 149° C. for 35 minutes, then cooled to ambient temperature. The measured solids content by Thermogravimetric Analysis (TGA) was 24 wt. % of PS-nanosilica.

Method of Measuring the Complex Shear Viscosity

A TA instruments Discovery Series HR-2 stress controlled rheometer with parallel plate geometry (obtained from TA Instruments, New Castle, Del.) was used to measure the complex shear viscosity. The tooling utilized an upper 40 millimeter (mm) top plate and a lower temperature controlled peltier plate. The gap between the upper and lower plate was 0.5 mm. The viscosity was measured by applying a 1% strain oscillation at a frequency of 1 Hz for 6 seconds, broken into a 3 second conditioning step and a 3 second measurement step.

Method of Measuring Cure Reaction Exotherm via Differential Scanning Calorimeter (DSC)

A TA Instruments Q Series DSC (obtained from TA Instruments, New Castle, Del.) was used to measure the dynamic heat flow of a material under application of a constant thermal ramp rate. Approximately 5 milligram (mg) of resin was weighed into an aluminum DSC pan. The sample pan was loaded into the DSC instrument, and the heat flow of the sample was measured in a dynamic DSC measurement with a thermal ramp rate of specified degree Celsius per minute (° C./min).

Method of Measuring the Dynamic Mechanical Properties Via a Dynamic Mechanical Analyzer (DMA)

A TA Instruments Q Series DMA (obtained from TA Instruments, New Castle, Del.) was used to measure low strain linear viscoelastic properties. Dynamic mechanical measurements were performed using single cantilever beam geometry. The low strain in-phase and out-of-phase deformation response was measured when applying a continuous oscillatory force with a controlled deformation amplitude of 20 micrometers (μm) at a frequency of 1 Hertz (Hz), and the resulting storage and loss moduli and loss tangent were calculated ramping the temperature during the measurement. The temperature was ramped at 3° C./min.

Method of Measuring Weight Loss Via Thermogravimetric Analysis (TGA)

A TA Instruments Q Series TGA (obtained from TA Instruments, New Castle, Del.) was used to measure the dynamic weight loss of a material under application of a constant thermal ramp rate. Samples of approximately 5 mg were loaded on platinum pans into the TGA. The mass loss of the sample was measured under a nitrogen atmosphere with a thermal ramp of 1° C./min.

Method of Measuring Fourier Transform Infrared (FTIR) Absorbance Spectroscopy

A Thermo Scientific Nicolet 6700 FTIR spectrometer with Smart iTR accessory (obtained from Thermo Fisher Scientific, Waltham, Mass.) was used to measure infrared absorbance by attenuated total reflectance (ATR). The spectral absorbance features that define the carbon-nitrogen triple bond stretch of the nitrile and the carbon-carbon double bond stretch of the allyl were measured for the phthalonitrile monomer system (resin+diluent) and the polymerized polymer network.

Method of Measuring Nuclear Magnetic Resonance (NMR) Spectroscopy

A Bruker Ultrashield 500 plus NMR spectrometer was used to measure the proton and carbon chemical shifts (obtained from Bruker, Billerica, Mass.). The proton and carbon chemical shifts are listed referenced to TMS. Integration of the proton resonance frequency absorption defined the number of protons observed. Proton and carbon chemical shifts and integration of the proton peaks were used to identify the material product.

Example Preparation

Comparative Examples A to E

Figure 2:
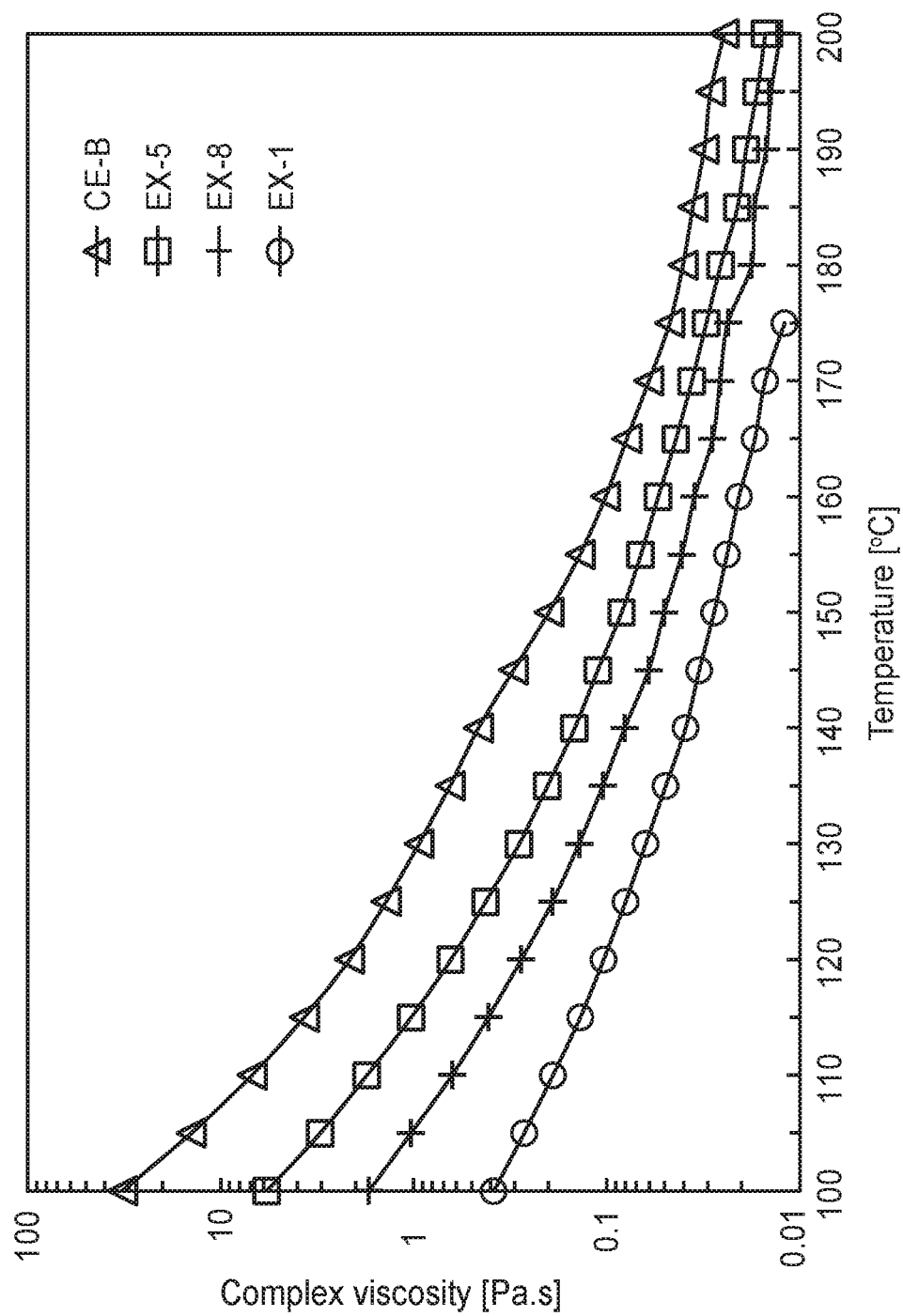
FIG. 2 is a plot of complex viscosity versus temperature for BMPN/RPN (2/1) [triangle] of Comparative Example B, BMPN/RPN (2/1) with 16.7% EuPN diluent [square] of Example 5, BMPN/RPN (2/1) with 33.3% tBPPN diluent [cross] of Example 8, BMPN/RPN (2/1) with 33.3% APPN diluent [circle] of Example 1.

Comparative Examples A to E (CE-A to CE-E) were prepared by first melt blending the phthalonitrile components in the amounts and at the temperature specified in Table 2. The complex shear viscosity for the CE-B phthalonitrile resin is shown in FIG. 2. 4,4'-(1,3-phenylenedioxy)dianiline was then added to the resin blend according to Table 2. The resulting resin was placed in an air circulating oven and cured as follows:

CE-A: 5 hours at 200° C. and 24 hours at 250° C., ramping 3° C./min between set points;

CE-B: 5 hours at 200° C. and 24 hours at 300° C., ramping 3° C./min between set points;

CE-C: 5 hours at 200° C., 24 hours at 300° C. and 6 hours at 325° C., ramping 3° C./min between set points;

CE-D: 5 hours at 200° C. and 24 hours at 300° C., ramping 3° C./min between set points; and CE-E: 5 hours at 200° C., 24 hours at 300° C., and 6 hours at 325° C. ramping 3° C./min between set points.

All comparative example resins underwent a thermosetting network polymerization to a hard stiff solid. The solid samples were then cooled at 5° C./min to 40° C. and removed from the aluminum pans. The samples were cut into strips for DMA measurement of the stiffness (E'), softening temperature (E' (onset)) and glass transition temperature (tan δ peak) in single cantilever beam geometry. The data for CE-A to CE-E is provided in Table 5.

The polymerization reaction of CE-B was followed by DSC measurement on a representative 5 mg sample. The sample was subjected to a thermal ramp with a heating rate of 0.25° C./min measuring the heat flow as a function of temperature. The mass specific heat of polymerization was calculated by integration of the reaction exotherm referenced to the base line heat flow of the material. The heat of polymerization is shown in Table 7.

was collected by vacuum filtration using a benchtop Buchner type filter with Whatman #4 filter paper and washed with 2000 mL of ambient temperature methanol/water (60/40 by mass). The liquid was collected and dried in a convection oven set at 120° C. The resin crystallized upon cooling. The product, 495 g (82.3%), had a melt temperature of 63° C. as measured by differential scanning calorimetry, and was identified as the desired compound by infrared and NMR analysis.

DSC $T_m$=63° C. FTIR (ATR; cm$^{-1}$): 2231 (—CN), 1639 (—C=C), 1247 (C—O—C). $^1$H NMR (500 MHz, CDCl$_3$ with 0.05% v/v TMS; δ, ppm): 7.72 (d, 1H), 7.37 (d, 1H), 7.31 (m, 2H), 7.21 (s, 1H), 7.19 (d, 1H), 6.99 (d, 1H), 5.84 (m, 1H), 5.02 (d, 1H), 4.96 (d, 1H), 3.28 (d, 2H). $^{13}$C NMR (500 MHz, CDCl$_3$ with 0.05% v/v TMS; δ, ppm): 161.79, 151.19, 135.42, 135.36, 132.42, 131.62, 128.54, 126.77, 121.09, 120.91, 120.86, 117.62, 116.75, 115.43, 115.01, 108.56, 34.08.

Preparatory Example 2 (PE-2), EuPN

EuPN, eugenol phthalonitrile (i.e., 4-(2-methoxy-4-allylphenoxy)phthalonitrile) was derived from the nucleophilic substitution reaction of 4-nitrophthalonitrile and eugenol (i.e., 2-methoxy-4-allylphenol). To a three necked 5000 mL reaction flask was added 400 g (2.31 mol) of 4-nitrophthalonitrile, 379.4 g (2.31 mol) of eugenol, 400 g (2.89 mol) of anhydrous K$_2$CO$_3$, and 2500 g of dry DMSO) and stirred for 48 hours at room temperature under a nitrogen atmosphere. The reaction solution was filtered through a Buchner funnel with Whatman #4 filter paper to remove undissolved salts. The filtered solution was added slowly to 4000 mL of ice

TABLE 2

CE-A to CE-E resin formulations

| Example* | Multifunctional Phthalonitrile Components | | | Aniline Component 4,4'-(1,3-Phenylenedioxy)dianiline | |
|---|---|---|---|---|---|
| | Material (wt ratio) | Amount, g | Temperature, ° C. | Amount, pph** | Temperature, ° C. |
| CE-A | BMPN | 9.0 | 190 | 4 | 190 |
| CE-B | BMPN/RPM (2:1) | 9.0 | 190 | 4 | 150 |
| CE-C | BMPN/RPN (1:1) | 9.0 | 190 | 4 | 190 |
| CE-D | BMPN/RPN/BTPN (4:1:1) | 9.0 | 190 | 4 | 190 |
| CE-E | BTPN | 9.0 | 190 | 4 | 190 |

*All comparative examples were prepared in a flat bottom 70 mm diameter thin gauge aluminum pan;
**pph = parts per hundred resin.

Preparatory Example 1 (PE-1), APPN

APPN, allylphenol phthalonitrile (i.e., 4-(2-allylphenoxy)phthalonitrile) was derived from the nucleophilic substitution reaction of 4-nitrophthalonitrile and 2-allylphenol. To a three necked 5000 milliliter (mL) reaction flask was added 400 g (2.31 mol) of 4-nitrophthalonitrile, 310.0 g (2.31 mol) of 2-allylphenol, 400 g (2.89 mol) of anhydrous K$_2$CO$_3$, and 2250 g of dry DMSO) and stirred for 48 hours at room temperature under a nitrogen atmosphere. The reaction solution was filtered through a Buchner funnel with Whatman #4 filter paper to remove undissolved salts. The filtered solution was added slowly to 4000 mL of cold methanol/water (60/40 by mass) cooled to a temperature below −25° C. that was mechanically stirred by a glass stir shaft fitted with a teflon stir blade. The temperature of the methanol/water solution was maintained below −15° C. during the addition of the reaction solution. Addition of the reaction solution resulted in precipitation of the product. The product cold methanol/water (60/40 by mass prepared by pouring 2080 g of methanol over 1400 g of ice) that was mechanically stirred by a glass stir shaft fitted with a teflon stir blade. Addition of the reaction solution resulted in precipitation of the product. The product was collected by vacuum filtration using a benchtop Buchner type filter with Whatman #4 filter paper and washed with 2000 mL of ambient temperature methanol/water (60/40 by mass). The product cake was scooped into an aluminum pan and placed in a convection oven set at 130° C. overnight to dry. The resin crystallized upon cooling. The product, 528 g (78.7%), had a melt temperature of 100° C. as measured by differential scanning calorimetry, and was identified as the desired compound by infrared and NMR analysis.

DSC $T_m$=100° C. FTIR (ATR; cm$^{-1}$): 2227 (—CN), 1636 (—C=C), 1244 (C—O—C). $^1$H NMR (500 MHz, CDCl$_3$ with 0.05% v/v TMS; δ, ppm): $^1$H NMR (500 MHz, CDCl$_3$ with 0.05% v/v TMS; δ, ppm): 7.69 (d, 1H), 7.18 (d, 1H), 7.17 (s, 1H), 7.02 (d, 1H), 6.88 (s, 1H), 6.85 (d, 1H), 5.99

(m, 1H), 5.16 (d, 1H), 5.13 (d, 1H), 3.77 (s, 3H), 3.43 (d, 2H). $^{13}$C NMR (500 MHz, CDCl$_3$ with 0.05% v/v TMS; δ, ppm): 161.94, 151.03, 140.01, 139.48, 136.65, 135.14, 122.33, 121.47, 120.46, 120.34, 117.29, 116.60, 115.62, 115.23, 113.34, 108.18, 55.76, 40.07.

Preparatory Example 3 (PE-3), tBPPN tBPPN, 4-tertbutylphenol phthalonitrile (i.e., 4-(4-tert-butylphenoxy)phthalonitrile) was derived from the nucleophilic substitution reaction of 4-nitrophthalonitrile and 4-tert-butylphenol. To a three necked 5000 mL reaction flask was added 300 g (1.73 mol) of 4-nitrophthalonitrile, 260.3 g (1.73 mol) of 4-tert-butylphenol, 300 g (2.17 mol) of anhydrous K$_2$CO$_3$, and 1900 g of dry DMSO) and stirred for 48 hours at room temperature under a nitrogen atmosphere. The reaction solution was filtered through a Buchner funnel with Whatman #4 filter paper to remove undissolved salts. The filtered solution was added slowly to 3000 mL of ice cold methanol/water (60/40 by mass prepared by pouring 1560 g of methanol over 1050 g of ice) that was mechanically stirred by a glass stir shaft fitted with a teflon stir blade. Addition of the reaction solution resulted in precipitation of the product. The product was collected by vacuum filtration using a benchtop Buchner type filter with Whatman #4 filter paper and washed with 1500 mL of ambient temperature methanol/water (60/40 by mass). The product cake was scooped into an aluminum pan and placed in a convection oven set at 130° C. overnight to dry. The resin crystallized upon cooling. The product, 429 g (89.6%), had a melt temperature of 120° C. as measured by differential scanning calorimetry, and was identified as the desired compound by infrared and NMR analysis.

DSC T$_m$=120° C. FTIR (ATR; cm$^{-1}$): 2231 (—CN), 1243 (C—O—C). $^1$H NMR (500 MHz, CDCl$_3$ with 0.05% v/v TMS; δ, ppm): $^1$H NMR (500 MHz, CDCl$_3$ with 0.05% v/v TMS; δ, ppm): 7.71 (d, 1H), 7.47 (d, 2H), 7.26 (s, 1H), 7.25 (d, 1H), 7.00 (d, 2H), 1.36 (s, 9H). $^{13}$C NMR (500 MHz, CDCl$_3$ with 0.05% v/v TMS; δ, ppm): 162.12, 151.02, 149.45, 135.33, 127.55, 121.33, 121.22, 120.10, 117.52, 115.49, 115.07, 108.47, 34.62, 31.40.

Preparatory Example 4 (PE-4), mCPN m-CPN, m-cresol phthalonitrile (i.e., 4-(3-methylphenoxy)phthalonitrile) was derived from the nucleophilic substitution reaction of 4-nitrophthalonitrile and m-cresol. To a three necked 5000 mL reaction flask was added 300 g (1.73 mol) of 4-nitrophthalonitrile, 187.4 g (1.73 mol) of m-cresol, 300 g (2.17 mol) of anhydrous K$_2$CO$_3$, and 1700 g of dry DMSO) and stirred for 48 hours at room temperature under a nitrogen atmosphere. The reaction solution was filtered through a Buchner funnel with Whatman #4 filter paper to remove undissolved salts. The filtered solution was added slowly to 3000 mL of ice cold methanol/water (60/40 by mass prepared by pouring 1560 g of methanol over 1050 g of ice) that was mechanically stirred by a glass stir shaft fitted with a teflon stir blade. Addition of the reaction solution resulted in precipitation of the product. The product was collected by vacuum filtration using a benchtop Buchner type filter with Whatman #4 filter paper and washed with 1500 mL of ambient temperature methanol/water (60/40 by mass). The product cake was scooped into an aluminum pan and placed in a convection oven set at 130° C. overnight to dry. The resin crystallized upon cooling. The product, 340 g (83.9%), had a melt temperature of 95° C. as measured by differential scanning calorimetry, and was identified as the desired compound by infrared and NMR analysis.

DSC T$_m$=95° C. FTIR (ATR; cm$^{-1}$): 2228 (—CN), 1247 (C—O—C). $^1$H NMR (500 MHz, CDCl$_3$ with 0.05% v/v TMS; δ, ppm): $^1$H NMR (500 MHz, CDCl$_3$ with 0.05% v/v TMS; δ, ppm): 7.72 (d, 1H), 7.35 (t, 1H), 7.25 (s, 1H), 7.24 (d, 1H), 7.13 (d, 1H), 6.89 (s, 1H), 6.87 (d, 1H), 2.40 (s, 3H). $^{13}$C NMR (500 MHz, CDCl$_3$ with 0.05% v/v TMS; δ, ppm): 161.95, 153.47, 141.19, 135.35, 130.37, 127.11, 121.42, 121.38, 121.20, 117.58, 117.56, 115.45, 115.02, 108.60, 21.39.

Examples 1 to 12 (EX-1 to EX-12)

Examples 1 to 12 (EX-1 to EX-12) were prepared by first melt blending the multifunctional phthalonitrile components in the amounts and at the temperature specified in Table 3. The resin was then cooled before adding the diluent phthalonitrile components in the amounts listed in Table 3 and stirred until homogenous. The complex shear viscosity for each of EX-1, EX-5, and EX-8 of the phthalonitrile resin is shown in FIG. 2. Finally, 4 parts per hundred resin (pph) of 4,4'-(1,3-phenylenedioxy)dianiline was then added to the resin blend at 150° C. and stirred until homogeneous (except for EX-11 and EX-12, which were stirred at 175° C. and 190° C., respectively). The resulting resin was placed in an air circulating oven and polymerized as follows:

EX-1 to EX-7: 3 hours at 175° C., 3 hours at 200° C. and 4 hours at 300° C., ramping 3° C./min between set points;

EX-8 and EX-9: 3 hours at 175° C., 3 hours at 200° C. and 24 hours at 300° C., ramping 3° C./min between set points;

EX-10 and EX-11: 3 hours at 175° C., 3 hours at 200° C., 4 hours at 300° C., and 2 hours at 325° C. ramping 3° C./min between set points;

EX-12: 3 hours at 175° C., 3 hours at 200° C., and 24 hours at 300° C., and 4 hours at 325° C. ramping 3° C./min between set points;

The polymerization reaction for each of EX-1 to EX-12 was followed by DSC on a representative 5 mg sample showing completion of the polymerization heat of reaction over the prescribed heating schedule. The monomer resins underwent a thermosetting network polymerization to a hard stiff solid. The solids were cooled at 5° C./min to 40° C. and removed from the aluminum pans. The samples were cut into strips for DMA measurement of the stiffness (E'), softening temperature (E' (onset)) and glass transition temperature (tan δ peak) in single cantilever beam geometry. The data for EX-1 to EX-12 are provided in Table 5.

The polymerization reaction of EX-1 and EX-8 was followed by DSC on two representative 5 mg samples. The first sample followed the prescribed heating schedule for the resin system placed in the air convection oven showing completion of the polymerization heat of reaction. The second sample was subjected to a thermal ramp with a heating rate of 0.25° C./min measuring the heat flow as a function of temperature. The mass specific heat of polymerization was calculated by integration of the reaction exotherm referenced to the base line heat flow of the material. The heat of polymerization is shown in Table 7.

Examples 13 to 19 (EX-13 to EX-19)

Examples 13 to 19 (EX-13 to EX-19) were each prepared by first melt blending the phthalonitrile components in the amounts and at the temperature specified in Table 4. 4,4'-(1,3-phenylenedioxy)dianiline was then added to the resin blend and stirred at the specified temperature according to Table 4. The resulting resin was placed in an air circulating oven and polymerized as follows:

EX-13 to EX-19: 3 hours at 175° C., 3 hours at 200° C. and 4 hours at 300° C., ramping 3° C./min between set points.

The polymerization reactions were followed by DSC on a representative 5 mg sample showing completion of the polymerization heat of reaction over the prescribed heating schedule. The monomer resins underwent a thermosetting network polymerization to a hard stiff solid. The solids were cooled at 5° C./min to 40° C. and removed from the aluminum pans. The samples were cut into strips for DMA measurement of the stiffness (E'), softening temperature (E' (onset)) and glass transition temperature (tan δ peak) in single cantilever beam geometry. The data for EX-13 to EX-19 are provided in Table 6. The storage modulus for each of EX-13 to EX-19 measured while ramping temperature at 3° C./min is plotted in FIG. 1.

TABLE 3

EX-1 to EX-12 resin formulations

| Example* | Multifunctional Phthalonitrile Components | | | | Phthalonitrile Diluent Components | |
|---|---|---|---|---|---|---|
| | Material (wt ratio) | Amount, g | Melt blend temp, ° C. | Cooling temp, ° C. | Material | Amount, g |
| EX-1 | BMPN/RPN (2:1) | 6.0 | 190 | 150 | APPN | 3.0 |
| EX-2 | BMPN/RPN (1:1) | 6.0 | 190 | 150 | APPN | 1.5 |
| | | | | | EuPN | 1.5 |
| EX-3 | BMPN/RPN/BTPN (4:1:1) | 7.5 | 190 | 150 | EuPN | 1.5 |
| EX-4 | BMPN/RPN (3:1) | 6.0 | 190 | 150 | EuPN | 3.0 |
| EX-5 | BMPN/RPN (2:1) | 7.5 | 190 | 150 | EuPN | 1.5 |
| EX-6 | BMPN/RPN (3:1) | 6.0 | 190 | 150 | APPN | 3.0 |
| EX-7 | BMPN (1) | 6.0 | 165 | 150 | APPN | 3.0 |
| EX-8 | BMPN/RPN (2:1) | 6.0 | 190 | 150 | tBPPN | 3.0 |
| EX-9 | BMPN/RPN/BTPN (4:1:1) | 7.5 | 190 | 150 | mCPN | 1.5 |
| EX-10 | BTPN/RPN (2:1) | 6.0 | 190 | 150 | EuPN | 3.0 |
| EX-11 | BPPN/BTPN (1:1) | 7.5 | 230 | 175 | APPN | 1.5 |
| EX-12 | BTPN (1) | 6.0 | 190 | 190 | mCPN | 3.0 |

*All comparative examples were prepared in a flat bottom 70 mm diameter thin gauge aluminum pan.

TABLE 4

EX-12 to EX-19 resin formulations

| Example* | Phthalonitrile Components | | | Aniline Component | |
|---|---|---|---|---|---|
| | Material (mass ratio) | Amount, g | Melt blend temp, ° C. | 4,4'-(1,3-Phenylenedioxy)dianiline Amount, pph** | Temperature, ° C. |
| EX-13 | BMPN/EuPN (99:1) | 9.0 | 165 | 4 | 150 |
| EX-14 | BMPN/EuPN (95:5) | 9.0 | 165 | 4 | 150 |
| EX-15 | BMPN/EuPN (90:10) | 9.0 | 165 | 4 | 150 |
| EX-16 | BMPN/EuPN (83.3:16.7) | 9.0 | 165 | 4 | 150 |
| EX-17 | BMPN/EuPN (67.3:32.7) | 9.0 | 165 | 4 | 150 |
| EX-18 | BMPN/EuPN (66.2:33.8) | 9.0 | 165 | 4 | 150 |
| EX-19 | BMPN/EuPN (65:35) | 9.0 | 165 | 4 | 150 |

*All comparative examples were prepared in a flat bottom 70 mm diameter thin gauge aluminum pan;

**pph = parts per hundred resin

Example 20 (EX-20)

640 g of BMPN and RPN in a 2/1 mass ratio were weighed into a 200 mm by 260 mm aluminum pan and melted in an air convection oven set at 200° C. The resin blend was stirred until homogeneous. The BMPN/RPN blend was cooled to 150° C. by reducing the temperature of the oven. 320 g of APPN was added to the BMPN/RPN blend and stirred until homogeneous. 38.4 g of 4,4'-(1,3-phenylenedioxy)dianiline was added to the resin blend and stirred into the resin at 150° C. until homogeneous. The resin was poured into a four-zone twin screw extruder fitted with a heated pump and a 100 mm wide die at the extruder exit. Each extruder zone was heated to 120° C. The pump temperature was set to 105° C., and the die temperature was set at 65° C. The resin exiting the die was fed between two polyethylene terephthalate (PET) release liners and passed through two rollers to spread the extruded resin to a uniform coating. The line speed was calibrated to yield a resin film thickness of 5 mil (0.13 mm).

Example 21 (EX-21)

A prepreg was prepared in a laboratory relevant environment using the phthalonitrile resin blend of Example 20. One PET release liner was removed from the phthalonitrile resin blend film of Example 20, leaving the film supported on the second release liner. The phthalonitrile film was placed with the release liner side down on a 9"×9" (22.9 cm×22.9 cm) hot plate heated to a temperature of 70° C., where the phthalonitrile resin has a viscosity of 10 pascal-seconds (Pa·s). A 4.5"×6.5" (11.4 cm×16.5 cm) piece of HexForce C-370-8HS-6K-8HBG-IM IM7 (370 g/m² areal density) continuous carbon fiber fabric (Hexel Corporation (Stamford, Conn.)) was laid on the phthalonitrile film. A second PET release liner was laid on top of the carbon fiber fabric, creating a stack of PET release liner, phthalonitrile film, carbon fiber fabric, and PET release liner. The carbon fiber fabric was impregnated with the phthalonitrile resin film with the assistance of a Marshalltown 2 inch firm rubber seam roller. Hand pressure was applied to the roller. Continuous roller stokes were used across the top release liner to push air out of the fabric and impregnate the fabric with resin. The final article consisted of a continuous carbon fiber fabric impregnated with phthalonitrile resin blend of example 20 between two release liners.

Example 22 (EX-22)

400 g of BMPN, RPN and APPN resin was blended in a mass ratio and prepared in the manner described in Example 7. 4 parts per hundred resin (pph) of 4,4'-(1,3-phenylenedioxy)dianiline was added to the resin blend at 135° C., stirred until homogeneous, and allowed to cool to ambient temperature. The resin blend system was added to the injector cylinder of a 2100 cc Series® injector (from Radius Engineering, Inc., Souths Salt Lake, Utah). The solid resin was melted in the injector cylinder at 135° C. and degassed under vacuum (less than 0.1 Torr (13.33 Pa)) using an air mixer head for agitation. Fourteen layers of a 5 harness satin weave fabric of 6K HEXTOW IM7 CARBON FIBER (form Hexcel Corp., Stamford, Conn., under trade designation "HEXTOW IM7 CARBON FIBER"), stacked in a symmetric quasi-isotropic layup configuration, was placed in a closed metal mold. The internal dimensions of the two-part mold were 330 mm by 330 mm by 4 mm. The mold was held in a hot press with approximately 180 kN of clamping force (approximately 870 kPa clamping pressure). The mold was evacuated to less than 0.1 Torr (13.33 Pa) of absolute pressure and pre-heated to an injection temperature of 175° C. The injection was conducted with the injector cylinder heated to 135° C., a heated line from the injector cylinder to the mold heated to 175° C., and a mold temperature of 175° C. Vacuum of less than 0.1 Torr (13.3 Pa) was applied during the mold filling process. When resin was detected at the mold exit, the exit valve was closed. Resin was injected up to a pressure of 100 psi (690 kPa). The panel was cured 3 hours at 175° C. and 3 hours at 205° C. The panel was demolded and post-cured for 4 hours in an air convection oven at 300° C. The panel showed good overall quality with low porosity. Based on fabric properties and the measured panel thickness, the fiber volume fraction was estimated to be 67%.

Example 23 (EX-23)

240 g of BMPN, RPN and APPN resin was blended in a mass ratio and prepared in the manner described in Example 7 in a 5 L round bottle flask and allowed to cool to 90° C. The 5 L round bottom flask was placed on a buchi rotary evaporator with an oil bath temperature set at 90° C. 283.5 g of a PS-nanosilica suspension in a 1/1 by mass 1-methoxy-2-propanol/butyl acetate solvent system (0.378 mass fraction silica prepared by stripping the PS-nanosilica sol of water and back adding butyl acetate) was preheated to 90° C. and added to the phthalonitrile resin blend. The 1-methoxy-2-propanol and butyl acetate solvents were stripped from the PS-nanosilica/phthalonitrile mixture at a bath temperature of 90° C. controlling the flask pressure to prevent the solution from bumping. The initial pressure was set at 500 mbar and gradually reduced over the course of 3 hours to 50 mbar. After 3 hours, most of the solvent had been stripped from the PS-nanosilica/resin blend. The bath temperature was increased to 140° C. and stripped for an additional 3 hours. The flask was removed from the rotary evaporator and the nanosilica filled resin was removed from the flask by pouring and scraping with a rubber spatula. 4 parts per hundred (pph) of 4,4'-(1,3-phenylenedioxy)dianiline based on weight of the resin blend excluding the weight of the PS-nanosilica was added to the PS-nanosilica filled resin blend at 135° C. and stirred until homogeneous. The resin was degassed in a heated vacuum chamber at 135° C. to remove entrapped air. The resin was poured into a ⅛" thick plaque mold open at one end preheated to a temperature of 175° C. The plaque had been prior treated with FREKOTE 55NC mold release. The plaque was cured for 3 hours at 175° C. and 3 hours at 205° C. The partially cured resin plaque was removed from the mold and post cured at 300° C. for an additional 12 hours. The nanosilica loading was determined by TGA weight loss measurement to be 29 wt %. A specimen was cut from the plaque for DMA measurement of the stiffness (E'), softening temperature (E' (onset)), and glass transition temperature (tan δ peak) in single cantilever beam geometry. The measured stiffness at 25° C. was 3625 MPa; the E' (onset) temperature was 314° C.; and the tan δ peak temperature was 362° C.

TABLE 5

Polymer network properties of cured phthalonitrile resin blends with/without phthalonitrile reactive diluents

| Example | Cured PN Network Resin (wt ratio) | Diluent (wt%) | Curative | DMA (single cantilever, 3° C./min ramp) E' (25° C.) MPa | DMA Tg (E' onset) ° C. | DMA Tg (tan δ peak) ° C. | TGA (1° C./min ramp) 5% wt loss, N₂ ° C. |
|---|---|---|---|---|---|---|---|
| CE-A | BMPN | | 4,4'-(1,3-phenylenedioxy)dianiline | 2840 | 209 | 229 | — |
| CE-B | BMPN/RPN (2/1) | | 4,4'-(1,3-phenylenedioxy)dianiline | 3290 | 243 | 277 | 417 |
| CE-C | BMPN/RPN (1/1) | | 4,4'-(1,3-phenylenedioxy)dianiline | 3360 | 281 | 320 | — |
| CE-D | BMPN/RPN/BTPN (4/1/1) | | 4,4'-(1,3-phenylenedioxy)dianiline | 3000 | 240 | 270 | — |
| CE-E | BTPN | | 4,4'-(1,3-phenylenedioxy)dianiline | 2630 | 279 | 312 | — |
| EX-1 | BMPN/RPN (2/1) | APPN (33.3%) | 4,4'-(1,3-phenylenedioxy)dianiline | 2830 | 319 | 370 | 420 |
| EX-2 | BMPN/RPN (1/1) | APPN/EuPN (33%) | 4,4'-(1,3-phenylenedioxy)dianiline | 2860 | 342 | >400 | — |
| EX-3 | BMPN/RPN/BTPN (4/1/1) | EuPN (16.7%) | 4,4'-(1,3-phenylenedioxy)dianiline | 2520 | 323 | 361 | — |
| EX-4 | BMPN/RPN (3/1) | EuPN (33.3%) | 4,4'-(1,3-phenylenedioxy)dianiline | 2870 | 329 | >400 | — |
| EX-5 | BMPN/RPN (2/1) | EuPN (16.7%) | 4,4'-(1,3-phenylenedioxy)dianiline | 2970 | 335 | >400 | — |
| EX-6 | BMPN/RPN (3/1) | APPN (33.3%) | 4,4'-(1,3-phenylenedioxy)dianiline | 2710 | 302 | 352 | — |
| EX-7 | BMPN | APPN (33.3%) | 4,4'-(1,3-phenylenedioxy)dianiline | 2940 | 290 | 350 | — |
| EX-8 | BMPN/RPN (2/1) | tBPPN (33.3%) | 4,4'-(1,3-phenylenedioxy)dianiline | 2940 | 188 | 208 | 386 |
| EX-9 | BMPN/RPN/BTPN (4/1/1) | mCPN (16.7%) | 4,4'-(1,3-phenylenedioxy)dianiline | 2500 | 208 | 232 | — |
| EX-10 | BTPN/RPN (2/1) | EuPN (33.3%) | 4,4'-(1,3-phenylenedioxy)dianiline | 2600 | 363 | >400 | — |
| EX-11 | BPPN/BTPN (1/1) | APPN (16.7%) | 4,4'-(1,3-phenylenedioxy)dianiline | 2480 | 329 | 365 | — |
| EX-12 | BTPN | mCPN (33.3%) | 4,4'-(1,3-phenylenedioxy)dianiline | 2680 | 242 | 270 | — |

TABLE 6

Polymer network properties of cured BMPN resin blends varying the concentration of EuPN reactive diluents

| Example | Resin | Diluent (wt%) | Resin:Diluent molar ratio | Curative | DMA (single cantilever, 3° C./min ramp) E' (25° C.) MPa | DMA Tg (E' onset) ° C. | DMA Tg (tan δ peak) ° C. | TGA (1° C./min ramp) 5% wt loss, N₂ ° C. |
|---|---|---|---|---|---|---|---|---|
| CE-A | BMPN | | | 4,4'-(1,3-phenylenedioxy)dianiline | 2840 | 209 | 229 | 417 |
| EX-13 | BMPN | EuPN (1.0%) | 47.2:1 | 4,4'-(1,3-phenylenedioxy)dianiline | 2650 | 220 | 237 | — |
| EX-14 | BMPN | EuPN (5.0%) | 9.20:1 | 4,4'-(1,3-phenylenedioxy)dianiline | 2450 | 254 | 276 | — |
| EX-15 | BMPN | EuPN (10.0%) | 4.32:1 | 4,4'-(1,3-phenylenedioxy)dianiline | 2450 | 276 | 305 | — |
| EX-16 | BMPN | EuPN (16.7%) | 2.44:1 | 4,4'-(1,3-phenylenedioxy)dianiline | 2490 | 279 | 317 | 417 |

TABLE 6-continued

Polymer network properties of cured BMPN resin blends varying the concentration of EuPN reactive diluents

| | Cured PN Network | | | | DMA (single cantilever, 3° C./min ramp) | | | TGA (1° C./min ramp) |
|---|---|---|---|---|---|---|---|---|
| | | Resin: | | | | | | |
| Example | Resin | Diluent (wt%) | Diluent molar ratio | Curative | E' (25° C.) MPa | Tg (E' onset) ° C. | Tg (tan δ peak) ° C. | 5% wt loss, N₂ ° C. |
| EX-17 | BMPN | EuPN (32.7%) | 1.00:1 | 4,4'-(1,3-phenylenedioxy)dianiline | 2890 | 278 | 342 | 405 |
| EX-18 | BMPN | EuPN (33.8%) | 0.95:1 | 4,4'-(1,3-phenylenedioxy)dianiline | 2940 | 278 | 342 | — |
| EX-19 | BMPN | EuPN (35.0%) | 0.90:1 | 4,4'-(1,3-phenylenedioxy)dianiline | 2550 | 299 | 360 | 403 |

TABLE 7

Differential scanning calorimetry measurement of the heat of polymerization

| | Cured PN Network | | | DSC (0.25° C./min ramp) Heat of polymerization J/g |
|---|---|---|---|---|
| Example | Resin (wt ratio) | Diluent (wt %) | Curative | |
| CE-B | BMPN/RPN (2/1) | | 4,4'-(1,3-phenylenedioxy)dianiline | 235 |
| EX-1 | BMPN/RPN (2/1) | APPN (33.3%) | 4,4'-(1,3-phenylenedioxy)dianiline | 330 |
| EX-8 | BMPN/RPN (2/1) | tBPPN (33.3%) | 4,4'-(1,3-phenylenedioxy)dianiline | 234 |

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A resin blend comprising at least one diluent comprising a single phthalonitrile functional group; and at least one diphthalonitrile resin, wherein the at least one diluent comprises a compound of formula I:

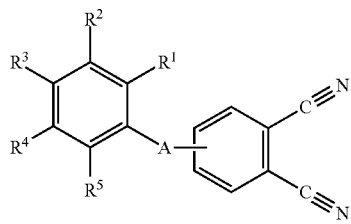

I wherein $R^1$, $R^2$, $R^3$, $R^4$, and $R^5$ are independently selected from H, an allyl group, a $C_1$ to $C_{20}$ alkyl group, an aryl group, an ether group, a thioether group, an aldehyde group, a ketone group, an ester group, an amide group, an acid group, a sulfonyl, a halogen, a nitro, a secondary amine group, a tertiary amine group, or a combination thereof with the proviso that one or more of $R^1$, $R^2$, $R^3$, $R^4$, and $R^5$ is an allyl group; and wherein A is oxygen or sulfur.

2. The resin blend of claim 1, wherein the at least one diluent comprises a compound of formula II:

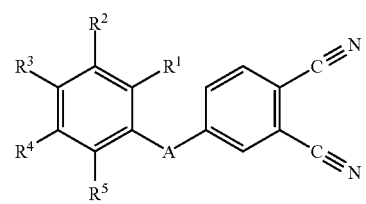

II wherein $R^1$, $R^2$, $R^3$, $R^4$, $R^5$, and A are each as defined with respect to formula I.

3. The resin blend of claim 1, wherein $R^1$ or $R^3$ is an allyl group.

4. The resin blend of claim 1, wherein A is oxygen.

5. The resin blend of claim 1, wherein the at least one diluent comprises at least one of 4-(2-methoxy-4-allylphenoxy)phthalonitrile or 4-(2-allylphenoxy)phthalonitrile.

6. The resin blend of claim 1, wherein the molar ratio of at least one diphthalonitrile resin to the at least one diluent ranges from 0.95 to 50, inclusive.

7. The resin blend of claim 1, wherein the at least one diphthalonitrile resin comprises a bisphenol M diphthalonitrile ether resin, a bisphenol P diphthalonitrile ether resin, a bisphenol T diphthalonitrile ether resin, or a combination thereof.

8. The resin blend of claim 1, further comprising a resorcinol diphthalonitrile ether resin.

9. The resin blend of claim 1, further comprising a filler.

10. The resin blend of claim 9, wherein the filler comprises at least one of reinforcing continuous fibers or reinforcing discontinuous fibers.

11. The resin blend of claim 9, comprising a nanofiller in an amount of 1 weight percent to 40 weight percent, inclusive, based on the total weight of the resin blend.

12. The resin blend of claim 9, comprising a microfiller in an amount of 1 weight percent to 90 weight percent, inclusive, based on the total weight of the resin blend.

13. The resin blend of claim 1, further comprising at least one additive selected from a catalyst, a curative, a toughening agent, and combinations thereof.

14. A prepreg comprising continuous reinforcing fibers and the resin blend of claim 1 impregnated into the continuous reinforcing fibers.

15. A prepreg comprising a cloth and the resin blend of claim 1 impregnated into the cloth.

16. A molding compound comprising chopped reinforcing fibers distributed in the resin blend of claim 1.

17. An article comprising a polymerization product of the resin blend of claim 1.

18. An article comprising a substrate and a layer of the resin blend of claim 1 disposed on the substrate.

* * * * *